(12) United States Patent  (10) Patent No.: US 8,460,940 B2
Menzel et al.  (45) Date of Patent: Jun. 11, 2013

(54) METHOD FOR ANALYSING A COMPLEX SAMPLE BY MASS SPECTROMETRY

(75) Inventors: Christoph Menzel, Hilden (DE); Christian Feckler, Aachen (DE); Udo Roth, Hilden (DE); Kerstin Steinert, Langenfeld (DE)

(73) Assignee: Qiagen GmbH, Hilden (DE)

(*) Notice: Subject to any disclaimer, the term of this patent is extended or adjusted under 35 U.S.C. 154(b) by 28 days.

(21) Appl. No.: 13/058,998

(22) PCT Filed: Aug. 14, 2009

(86) PCT No.: PCT/EP2009/005905
§ 371 (c)(1),
(2), (4) Date: May 9, 2011

(87) PCT Pub. No.: WO2010/017995
PCT Pub. Date: Feb. 18, 2010

(65) Prior Publication Data
US 2011/0207227 A1   Aug. 25, 2011

(30) Foreign Application Priority Data
Aug. 15, 2008 (EP) .................... 08014583

(51) Int. Cl.
*G01N 33/68* (2006.01)
*G01N 33/48* (2006.01)
*G01N 24/00* (2006.01)

(52) U.S. Cl.
USPC ............... 436/86; 436/63; 436/173; 436/174; 250/281; 250/282

(58) Field of Classification Search
USPC .............. 436/63, 86, 173, 174, 177; 250/281, 250/282
See application file for complete search history.

(56) References Cited

U.S. PATENT DOCUMENTS

2006/0121599 A1* 6/2006 Reihs .......................... 435/287.1
2008/0108144 A1* 5/2008 Alam et al. ..................... 436/66
2008/0213277 A1* 9/2008 Sasu et al. .................. 424/141.1

FOREIGN PATENT DOCUMENTS
WO    WO2004/055857    7/2004

OTHER PUBLICATIONS

Poetsch et al. Journal of Biomolecular Techniques, vol. 19, Apr. 2008, pp. 129-138.*
Roberts et al. Abstract from Gastroenterology, vol. 134, No. 4, suppl. 1, pp. A447, Apr. 2008.*
Anderson et al. Analytical Chemistry, vol. 82, Feb. 15, 2010, pp. 1551-1555.*

(Continued)

*Primary Examiner* — Maureen Wallenhorst
(74) *Attorney, Agent, or Firm* — Fanelli Haag & Kilger PLLC

(57) ABSTRACT

A mass spectrometry method for analysing the presence or absence of at least one target analyte in a complex sample is provided. The method uses a sample carrier suitable for mass spectrometry with a pre-applied microcrystalline MALDI matrix spot which is at least partially encompassed by a hydrophobic region. A complex sample is applied such that it becomes located on the microcrystalline MALDI matrix spot. The sample is washed on the microcrystalline MALDI matrix spot and then analyzed for the presence or absence of at least one target analyte via mass spectrometry. The method is in particular suitable for quantitatively analysing target analytes such as hepcidin and other peptides, drug compounds and metabolites in body fluids.

12 Claims, 21 Drawing Sheets

OTHER PUBLICATIONS

Figure 1:
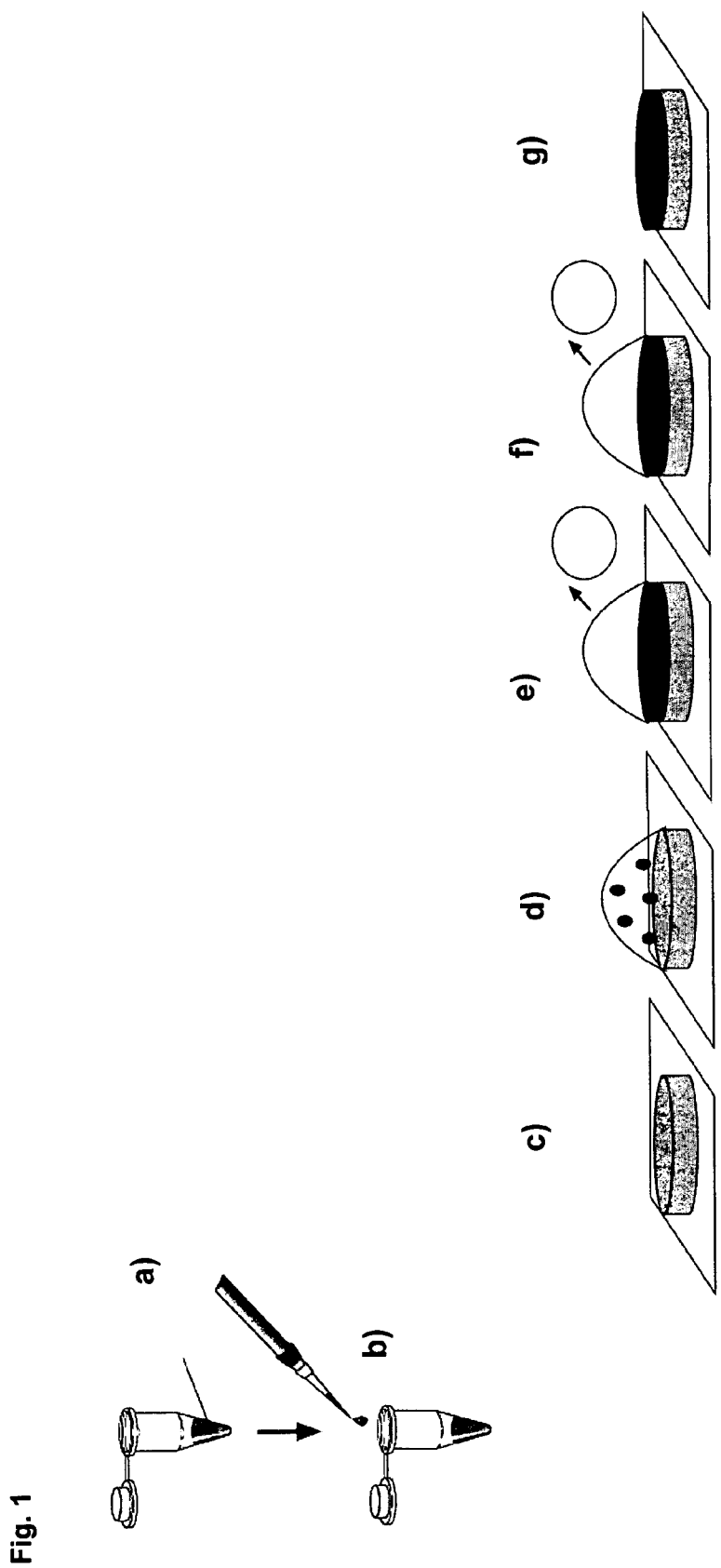

Gobom, et al., "Alpha-cyano-4-hydroxycinnamic acid affinity sample preparation. A protocol for MALDI-MS peptide analysis in proteomics", Analytical Chemistry, American Chemical Society, Columbus, US, vol. 73, No. 3, Dec. 28, 2000, pp. 434-438.

Jaloi, et al., "The proteolysis-inducing factor: in search of its clinical relevance in patients with metastatic gastric/esophageal cancer", Diseases of the Esophagus: Official Jaurnal of The International Society for Diseases of the Esophagus/I.S.D.E 2006, vol. 19, No. 4, 2006, pp. 241-247.

Su, et al., "Rapid drug-screening and quantitation of 3,4-methylenedioxymethamphet amine in urine by MALDI-TOP mass spectrometry" Analytica Chimica Acta, Elsevier, Amsterdamn, NL, vol. 546, No. 2, Aug. 8, 2005, pp. 193-198.

Swinkels, et al., "Advances in quantitative hepcidin measurements by time-of-flight mass spectrometry" PLOS One 2008, vol. 3, No. 7, 2008, pp. E2706.

Roberts, et al., "M1996 Hepcidin Expression Relates to Colorectal Tumour Stage" Gastroenterology, Elsevier, Philadelphia, PA, vol. 134, No. 4, Apr. 1, 2008, pp. A-447.

Ward, et al., "Proteomic profiling of urine for the detection of colon cancer" Proteome Science, vol. 6, Jun. 2008, pp. 1-15.

International Search Report of PCT/EP2009/005905, Dated Apr. 11, 2009.

* cited by examiner

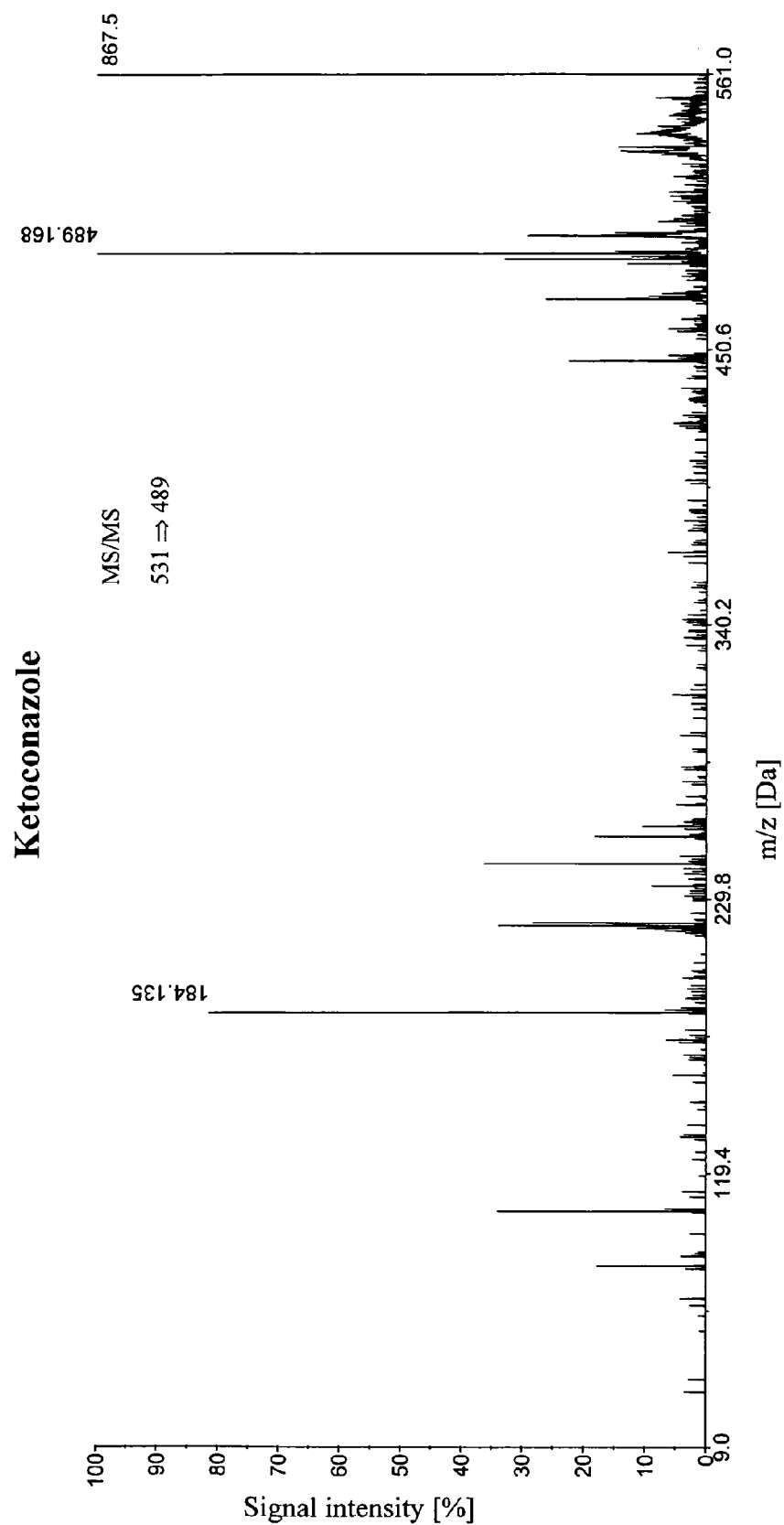

SEQUENCE LISTING

```
<160> NUMBER OF SEQ ID NOS: 8

<210> SEQ ID NO 1
<211> LENGTH: 25
<212> TYPE: PRT
<213> ORGANISM: Homo sapiens
<220> FEATURE:
<221> NAME/KEY: DISULFID
<222> LOCATION: (7)..(23)
<220> FEATURE:
<221> NAME/KEY: DISULFID
<222> LOCATION: (10)..(22)
<220> FEATURE:
<221> NAME/KEY: DISULFID
<222> LOCATION: (11)..(19)
<220> FEATURE:
<221> NAME/KEY: DISULFID
<222> LOCATION: (13)..(14)

<400> SEQUENCE: 1

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 2
<211> LENGTH: 22
<212> TYPE: PRT
<213> ORGANISM: Homo sapiens
<220> FEATURE:
<221> NAME/KEY: DISULFID
<222> LOCATION: (4)..(20)
<220> FEATURE:
<221> NAME/KEY: DISULFID
<222> LOCATION: (7)..(19)
<220> FEATURE:
<221> NAME/KEY: DISULFID
<222> LOCATION: (8)..(16)
<220> FEATURE:
<221> NAME/KEY: DISULFID
<222> LOCATION: (10)..(11)

<400> SEQUENCE: 2

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 3
<211> LENGTH: 20
<212> TYPE: PRT
<213> ORGANISM: Homo sapiens
<220> FEATURE:
<221> NAME/KEY: DISULFID
<222> LOCATION: (2)..(18)
<220> FEATURE:
<221> NAME/KEY: DISULFID
<222> LOCATION: (5)..(17)
<220> FEATURE:
<221> NAME/KEY: DISULFID
<222> LOCATION: (6)..(14)
```

```
<220> FEATURE:
<221> NAME/KEY: DISULFID
<222> LOCATION: (8)..(9)

<400> SEQUENCE: 3

Ile Cys Ile Phe Cys Cys Gly Cys Cys His Arg Ser Lys Cys Gly Met
1               5                   10                  15

Cys Cys Lys Thr
            20

<210> SEQ ID NO 4
<211> LENGTH: 4
<212> TYPE: PRT
<213> ORGANISM: Homo sapiens
<220> FEATURE:
<221> NAME/KEY: SITE
<222> LOCATION: (1)..(4)
<223> OTHER INFORMATION: N-terminal sequence tag determined by MS/MS
<220> FEATURE:
<221> NAME/KEY: SITE
<222> LOCATION: (1)..(4)
<223> OTHER INFORMATION: N-terminal sequence tag of HEPC-25

<400> SEQUENCE: 4

Asp Thr His Phe
1

<210> SEQ ID NO 5
<211> LENGTH: 18
<212> TYPE: PRT
<213> ORGANISM: Homo sapiens
<220> FEATURE:
<221> NAME/KEY: Site
<222> LOCATION: (1)..(1)
<223> OTHER INFORMATION: restriction site for trypsin after arginin (not
      shown, located before serin in position 1 of this sequence - see
      Fig. 5b)
<220> FEATURE:
<221> NAME/KEY: Site
<222> LOCATION: (18)..(18)
<223> OTHER INFORMATION: restriction site for trypsin after arginin
      (position 18 of this sequence - see Fig. 5b)

<400> SEQUENCE: 5

Ser Gly Ser Val Ile Asp Gln Ser Arg Val Leu Asn Leu Gly Pro Ile
1               5                   10                  15

Thr Arg

<210> SEQ ID NO 6
<211> LENGTH: 15
<212> TYPE: PRT
<213> ORGANISM: Homo sapiens

<400> SEQUENCE: 6

Val Arg Tyr Thr Lys Lys Val Pro Gln Val Ser Thr Pro Thr Leu
1               5                   10                  15

<210> SEQ ID NO 7
<211> LENGTH: 16
<212> TYPE: PRT
<213> ORGANISM: Homo sapiens

<400> SEQUENCE: 7

Leu Val Arg Tyr Thr Lys Lys Val Pro Gln Val Ser Thr Pro Thr Leu
1               5                   10                  15

<210> SEQ ID NO 8
<211> LENGTH: 24
```

```
<212> TYPE: PRT
<213> ORGANISM: Homo sapiens

<400> SEQUENCE: 8

Asp Ala His Lys Ser Glu Val Ala His Arg Phe Lys Asp Leu Gly Glu
1               5                   10                  15

Glu Asn Phe Lys Ala Leu Val Leu
            20
```

METHOD FOR ANALYSING A COMPLEX SAMPLE BY MASS SPECTROMETRY

The analysis of molecules and/or biological material is of importance not only for research purposes put also for in-vitro diagnostic detection and/or quantitation methods. Several methods are established in the prior art for analysing different molecules in different samples. E.g. small molecules such as metabolites or drugs are regularly analysed e.g. by mass spectrometry; peptides and proteins by methods such as mass spectrometry or immunoassays (e.g. ELISA); nucleic acids are also often analysed by PCR and to a lower extent by mass spectrometry. One preferred mass spectrometric method for analysing molecules and in particular biological molecules in the samples is matrix-assisted laser desorption/ionisation mass spectrometry (MALDI-MS).

One prominent example of an important biological target analyte for diagnostic purposes is the peptide hepcidin (HEPC). Mature active hepcidin (25 amino acids, 2787 Da) is a liver expressed cysteine-rich disulfide-bridged peptide hormone and a key regulator of iron metabolism. It exists in several isoforms with differing biological activity (e.g. active, mature HEPC 25 and the truncated forms HEPC 20 and HEPC 22 with no known biological activity). The concentration of hepcidin in urine or blood provides diagnostic value in frequent aberrations of iron homeostasis such as hemochromatosis, thalassemia or aneamia of chronic disease (e.g. in cancer, diabetes, or rheumatism). The precise measurement of hepcidin levels is also highly relevant in pharmacokinetic studies on therapeutics agonizing or antagonizing hepcidin excretion. Due to its key role in iron homeostasis, the quantitation of hepcidin is essential to better understand the relationship to other iron related proteins such as transferrin, ferritin, hemojuvelin or ferroportin. In this context its accurate measurement is crucial to decipher not yet understood iron related biochemical pathways. The detection and quantification of serum or urinary hepcidin is, however, hampered due to the lack of appropriate assay methods (see e.g. Kemna (2008) p. 93 or Malyszko (2007) p. 27). Common immunochemical methods are regarded as problematic mainly because of the lack of suitable hepcidin specific antibodies. These antibodies are difficult to obtain, due to the small size of hepcidin, the compact and complex structure of the molecule, and the highly conserved sequence among species, complicating the elicitation of an immune response in the host species. Furthermore, an antibody based assay will probably not be able to distinguish between the at least three different truncated Hepcidin isoforms detectable in serum/urine, having widely differing biological activity. So far only ELISA methods are available for detecting prohepcidin in serum. However, serum prohepcidin levels do not correlate well with the mature hormone and respective assays are accordingly not sufficiently accurate. Other hepcidin assays rely on mRNA expression analysis, preferably in animal and cell culture models. However, this kind of analysis does not give direct information on the concentration of the active hormone in urine or serum/plasma, nor are tissue expression experiments due to their invasive nature adequate for clinical studies in humans.

Also mass spectrometry assays were developed for analyzing hepcidin. One approach uses the SELDI technique (Kemna (2005b) & (2007); Tomosugi (2006)) using IMAC and Normal Phase (NP) SELDI surfaces. However, the sensitivity is not yet sufficient to detect decreased Hep-25 levels for pathological conditions such as hemochromatosis. Furthermore, the SELDI technique is a rather time-consuming, which hampers the quick analysis of samples in particular in a high throughput format.

Also MALDI-MS using standard dried droplet preparation has been tried for analyzing hepcidin in urine samples form colorectal cancer patients (Ward (2008)). However, the standard sample preparation method requires the massive dilution or desalting of the sample prior to applying said sample, e.g. by using reversed-phase magnetic beads. This limits the detection and the overall throughput due to the necessity of additional steps. A further method relies on a liquid chromatography tandem mass spectrometry assay (LC-MS/MS) for determining serum hepcidin. However, this technique uses various means of sample preparation prior to the analysis to purify the target molecules, which decreases the overall throughput Furthermore, the LC-MS/MS methods needs large quantities namely at least 50 ml sample volume.

Also the analysis of small molecules such as endogenous metabolites or drug compounds respectively their metabolites is important. An important high throughput clinical diagnostic application is the screening for metabolic disorders in newborns by quantification of endogenous metabolites such as specific amino acids or carnitines. This screening allows the early diagnosis of amino acidemias (e.g. phenylketonuria (PKU)), and/or organic acidemias (e.g. propionic acidemia (PA)) and/or fatty acid oxidation disorders (e.g. medium-chain acyl-CoA dehydrogenase (MCAD) deficiency) and guides the treatment or intervention, which substantially improves the clinical outcome of the diseases.

An important clinical diagnostic example for the quantitative measurement of drug compounds and their metabolites is the therapeutic drug monitoring e.g. for antiretroviral drugs employed in anti-HIV therapy or for immunosuppresive drugs after organ transplantation. Immunosuppressive therapy is the most crucial treatment of organ-transplanted patients, as lower levels of these drugs are associated with insufficient therapy and eventually result in rejection of the organ, and, on the contrary, higher levels are associated with life-threatening toxicity to certain organs such as liver and kidneys. More than 25.000 patients receive every year in the US a solid organ transplant with more than 90.000 Americans on the waiting lists. Nearly all of these patients would have required extensive drug monitoring early after transplantation and will require frequent monitoring for the remainder of their lives while they receive these therapies summing up to millions of samples.

Respective assays for endogenous metabolites and drugs compounds are very often routinely performed by liquid chromatography (LC) coupled to single or tandem mass spectrometry (LC-MS/MS). For the mass spectrometric ionization, preferably electrospray (ESI) or atmospheric pressure chemical ionization (APCI) are employed. These techniques are used for example intensively in pharmacokinetics during drug development or in clinical laboratories to detect and quantitate accurately the concentration of small molecules from raw body liquids such as urine or blood serum (reviewed e.g. by Want 2005, Maurer 2005).

Selective and sensitive analytical methods for the quantitative evaluation of drugs and their metabolites are critical for the successful conduct of preclinical, biopharmaceutical and/or clinical pharmacological studies. Bioanalytical method validation includes all of the procedures that demonstrate that a particular method used for quantitative measurement of analytes in a given biological matrix, such as blood, plasma, serum, or urine, is reliable and reproducible for the intended use. The fundamental parameters for this validation include (1) accuracy, (2) precision, (3) selectivity, (4) sensitivity, (5)

reproducibility, and (6) stability. Validation involves documenting, through the use of specific laboratory investigations, that the performance characteristics of the method are suitable and reliable for the intended analytical applications. The acceptability of analytical data corresponds directly to the criteria used to validate the method.

Albeit it is possible to quantitate many compounds in parallel with LC-MS/MS by methods such as multiple reaction monitoring (MRM), the LC separation needs for an individual sample typically 3-5 minutes, limiting the overall sample throughput. As a consequence in high throughput applications very often several instruments are employed in parallel, which increases the costs of the analysis. Additionally, as the HPLC is typically not able to work directly with unpurified body liquids one or more complex sample preparation steps are additionally needed, which further limits the throughput. The most common of these pre-treatment methods are summarised in the following:

Solid Phase Extraction (SPE) is the most frequently used method today to extract and clean-up small molecules from biological samples. Purification is based on various chromatographic methods such as reverse phase, normal phase or ion exchange media depending on the target molecule. The method can be automated for example via 96 well plates and vacuum manifolds. Major disadvantages of the SPE approach are the time for the extra sample prep step and the extra costs for the disposables.

Liquid/liquid extraction (LLE) of small molecules is achieved via solvent extraction and partitioning. LLE is hence a method to separate compounds based on their relative solubility in two different immiscible liquids, usually water and an organic solvent. It is an extraction of a substance from one liquid phase into another liquid phase. The time-consuming protocols need to be optimized for each new compound and biological matrix and are typically difficult to automate, albeit some automation approaches can be found in the scientific literature.

Protein precipitation (PP) allows the clean-up of biological samples from contaminating proteins by protein precipitation. In the context of small molecule analysis PP is frequently performed with organic buffers such as methanol or acetonitrile, which are compatible with the mobile phase of the consecutive LC step. PP is also often combined with SPE or LLE for a more effective target molecule clean-up accompanied by a further increase in time and labor and material costs.

The dilution of the sample is a further common approach. Direct injection particularly of diluted plasma and urine samples into the LC system has become a more popular technique as researchers attempt to increase sample throughput ("dilute-and-shoot approach"). The technique is supported by the high robustness of some modern LC column materials against particle contaminations (clogging) and the higher sensitivity of modern mass spectrometers. Nevertheless, the major disadvantage is the reduced sensitivity for critical assays due to the dilution step and the still high biological matrix background, which may lead to increased "matrix effects" with unwanted signal suppression or enhancement as the target analytes are not enriched.

MALDI mass spectrometry is mostly used for the analysis of macromolecules above 700-800 Da combined with time-of-flight (TOF) mass analyzers. The major drawback for the analysis of small molecules is the large interfering matrix ion background from most MALDI matrices and the inferior quantitation properties features of TOF analyzers. Furthermore, also for MALDI most samples must undergo complex pre-treatment steps prior to the actual analysis by mass spectrometry, as also MALDI does so far not allow the direct analysis from complex samples such as raw/crude body liquids. In consequence all of the above classical up-front sample preparation techniques for LC-MS/MS are typically also applied for small molecule clean-up prior to MALDI-MS with or without LC separation. In any case does the up-front sample preparation negatively affect the overall achieved assay throughput and adds substantially to the costs per analysis.

It is the object of the present invention to provide an improved method for analysing analytes, in particular endogenous peptides such as hepcidin and small molecules such as drug compounds in a sample, which allows the analysis of complex samples, in particular unpurified body fluids.

A further object of the present invention is to provide a fast and sensitive method for detecting hepcidin in a complex sample.

According to a first embodiment a mass spectrometry method for analysing the presence or absence and/or quantity of at least one analyte in a complex sample is provided, comprising at least the following steps:
  a) Using a sample carrier suitable for mass spectrometry comprising a pre-applied microcrystalline MALDI matrix spot which is at least partially encompassed by a hydrophobic region;
  b) Applying a complex sample such that it becomes located on said microcrystalline MALDI matrix spot;
  c) washing said sample on said microcrystalline MALDI matrix spot;
  d) analysing said sample for the presence or absence of at least one target analyte via mass spectrometry.

The method according to the present invention uses a microcrystalline MALDI matrix spot to clean up, detect and distinguish even minute amounts of analytes directly from complex samples. A "complex sample" as used herein is a sample which has at least one, preferably at least two or more of the following characteristics:
  a) it is a body fluid or component thereof such as urine, blood, serum, plasma, cerebrospinal fluid (CSF), sputum, amniotic fluid, bronchial lavage, lymph, semen, saliva, lacrimal fluid, pleural fluid, pulmonary fluid, synovial fluid, peritoneal fluid, abdominal fluid, bone marrow aspirate, nipple aspirate, breast milk; and/or
  b) it comprises more than 50 (or even more than 100, 150, 200, 500, 1000 or even more than several thousand) different compounds, including potential analytes such as peptides, metabolites, drug compounds and their metabolites, oligonucleotides e.g. DNA or RNA, glycoconjugates e.g. glycoproteins, glycopeptides, peptidoglycans, glycolipids, and lipopolysaccharides, proteins, e.g. abundant proteins such as albumins, immoglobulins; and/or
  c) it comprises salts and/or urea and/or carbohydrates and/or lipids in particular more than 100 mM (or even more than 150, 200, 250, 300, 350, 400, 450, 500 or more than 550 mM) salt and/or urea and/or carbohydrates and/or lipids; and/or
  d) it was not purified or separated prior to step b), in particular the term "it was not purified or separated prior to step b)" particularly refers to that said complex sample was not electrophoretically separated or purified e.g. by sodium dodecyl sulfate polyacrylamide gel electrophoresis (SDS-PAGE) and/or by capillary electrophoresis and/or free-flow electrophoresis; and/or said complex sample was not chromatographically separated or purified using e.g. solid phase extraction devices and/or high-performance liquid chromatography with reverse-phase, normal phase, ion-exchange, size-exclusion, ion metal affinity or other affinity media; and/or said complex sample was not separated or purified by liquid/liquid extraction; and/or said complex sample was not separated or purified by precipitation e.g. protein precipitation or reversible precipitation; and/or said complex sample was not separated or purified by ultrafiltration; and/or said complex sample was not separated or purified by isoelectric focusing.

Said complex sample may also comprise excipients or auxiliary incredients e.g. needed to obtain the body fluid or used as a carrier for active ingredients such as antiadherents, binders, coatings, disintegrants, fillers, diluents, flavours, colours, glidants, lubricants, preservatives, sorbents and/or sweeteners.

Respective samples and in particular body fluids are complex in their nature and often comprise high amounts of contaminants, which made it impossible or at least difficult using the prior art methods to directly analyse them by mass spectrometry without prior pre-treatment and in particular without prior purification and/or separation. The contaminants disturbing the mass spectrometric analysis vary widely based on the type of complex samples (e.g. when analysing samples derived from body fluids such as serum or urine). Typical contaminants include e.g. abundant proteins such as albumins, globulins and mucins as well as high concentrations of salt and/or urea. The method according to the present invention, however, allows the analysis of analytes in biological fluids and in particular complex body fluids such as urine, blood, serum, plasma, cerebrospinal fluid (CSF), sputum, amniotic fluid, bronchial lavage, lymph, semen, saliva, lacrimal fluid, pleural fluid, pulmonary fluid, synovial fluid, peritoneal fluid, abdominal fluid, bone marrow aspirate, nipple aspirate and/or breast milk. The method is in particular suitable to analyze the presence or absence of analytes particularly in urine, serum and/or plasma and/or CSF. Surprisingly, the method according to the present invention is robust and reproducible and allows the detection of minute amounts of analytes in complex samples, despite the presence of contaminants. The signal intensity is furthermore robust against differences in the concentration of contaminants. Also, not only a qualitative, but also a quantitative assay is feasible if desired, i.e. the signal intensity obtained with the method according to the present invention correlates to the concentration of the analyte in the body fluid. Furthermore, the method is simple to perform, as complex sample preparation steps become obsolete and the method is quick, thereby also allowing high throughput applications. This provides significant advantages over the prior art.

The method according to the present invention is particularly useful when the target analyte is selected from mature hepcidin 25, truncated hepcidin isoforms and/or prohepcidin. As is outlined in the introduction, the analysis of hepcidin in complex samples is a particular challenge and so far, this was not possible with conventional mass spectrometry methods. Thus, in the prior art it was necessary to e.g. dilute the samples (see e.g. Ward, 2008) or purify them what has drawbacks regarding the sensitivity. Surprisingly, the method according to the present invention allows the analysis/detection of hepcidin (this includes mature hepcidin 25 as well as truncated hepcidin isoforms such as hepcidin-22, hepcidin-20 and/or prohepcidin) in complex samples, such as body fluids (in particular urine, blood, plasma, serum and complex samples derived therefrom). Usually, a complex sample that is analysed in a hepcidin assay has one or more of the following characteristics:

a) it is or is derived from body fluids, in particular urine, blood, serum or plasma; and/or
b) it comprises more than 50 different compounds; and/or
c) it comprises more than 100 mM salt, urea, carbohydrates and/or lipids.

The method according to the present invention allows the reliable and reproducible detection of hepcidin in a complex sample, even if hepcidin is present at a low concentration. With the method according to the present invention, a limit of detection (LOD) is achieved that allows to determine hepcidin concentrations at diagnostically relevant levels in complex samples. Besides being sensitive, the method according to the present invention has the further advantage that is easy and quick to perform. Due to the few necessary sample preparation and processing steps, the throughput is significantly increased. At the same time, the error-proneness of the overall method is decreased.

According to one embodiment, the microcrystalline MALDI matrix spot which is used for the hepcidin analysis
a) comprises crystals having predominantly a crystal size of $\leq 5$ μm and
b) is obtained by a sublimation process.

It was shown that a homogenous MALDI matrix spot having a small crystal size can be obtained when the microcrystalline MALDI matrix spot is produced by a sublimation process (which is described in further detail below). The homogenous structure of a respectively produced microcrystalline MALDI matrix spot apparently advantageously influences the performance of the method according to the present invention. This is particularly advantageous when analysing hepcidin (this includes mature hepcidin 25 as well as truncated hepcidin isoforms such as hepcidin-22, hepcidin-20 and/or prohepcidin).

Further advantages and specific embodiments of the hepcidin assay according to the present invention are outlined in further detail below.

The mass spectrometry method of step d) preferably comprises laser desorption/ionization-type of mass spectrometry and in particular MALDI mass spectrometry such as vacuum or atmospheric pressure MALDI ion sources coupled to mass spectrometric analyzers such as linear or reflector time-of-flight analyzers (MALDI-TOF), quadrupole analyzers, quadrupole ion trap analyzers, linear ion trap analyzers, orbitrap analyzers, Fourier-transform ion cyclotron resonance (FT-ICR) analyzers or combinations thereof such as quadrupole-time-of-flight (qTOF) analyzers, tandem time-of-flight analyzers (TOF/TOF) or triple quadrupole (QqQ) analyzers.

According to one embodiment, the hydrophobic region which at least partially encompasses the microcrystalline MALDI matrix spots is oleophobic, lyophobic and preferably ultraphobic. An example of a suitable ultraphobic surface is disclosed in US 2006/0121599, see in particular paragraphs 18 and 19 and the references cited therein and WO 00/39240, which are hereby incorporated as references and thus count as part of the disclosure. A "hydrophobic" surface is understood as a water repellent surface, i.e. one resistant to wetting by aqueous solutions. Preferably, a hydrophobic surface has a contact angle of a drop of water lying on the hydrophobic surface of more than 90°. The term "oleophobic" refers to surfaces which repel or which can not be wetted by oil, respectively. An "ultraphobic surface" means a surface/region having a contact angle of a drop of water and/or oil lying on an ultraphobic surface of more than 150° preferably more than 160° and ideally 170° with a roll-off angle not exceeding 10°. Roll-off angle means the angle of inclination of a basically planar but structured surface from the horizontal, at which a stationary drop of water and/or oil with a volume of 10 μl is moved due to gravity, when the surface is inclined. Such ultraphobic surfaces are disclosed for example in US2006/0121599, WO 00/39240, WO 98/23549; WO 96/04123; WO 96/21523; WO 00/39369; WO 00/39368; WO 00/39229; WO 00/39051; WO 00/38845 and WO 96/34697, which are hereby incorporated as references and thus count as part of the disclosure regarding the ultraphobic surfaces.

The feature that the microcrystalline matrix spot is at least partially encompassed by a hydrophobic region defines a design, wherein the hydrophobic region is located adjacent and thus in close proximity to the microcrystalline matrix spot. Preferably, the hydrophobic region completely encompasses and thus surrounds the microcrystalline matrix spot. This has the effect that a sample droplet applied onto the sample carrier is due to the hydrophobic forces forced onto the microcrystalline matrix spot, if e.g. the sample droplet is not placed directly accurately onto said matrix spot. Several designs are feasible. According to one embodiment, the microcrystalline MALDI matrix spot is applied onto a hydrophobic surface layer or area, which is e.g. larger than the microcrystalline matrix spot. However, also different designs could be used, wherein e.g. the microcrystalline matrix spot is located in an opening of the hydrophobic region, which may be e.g. a hydrophobic layer covering the whole sample carrier or area thereof.

The microcrystalline MALDI matrix spot may have any shape and can be e.g. round, square or any other possible shape. The MALDI matrix spots are according to one embodiment deposited on the sample carrier and preferably onto a hydrophobic or even ultraphobic surface layer or area from the gas phase, preferably by a vacuum sublimation process. Therefore, according to one embodiment, the microcrystalline MALDI matrix spot is deposited onto the sample carrier by a vacuum sublimation process. Preferably, deposition occurs onto a hydrophobic or even ultraphobic surface layer. Suitable MALDI matrices are known in the prior art and also described herein. The MALDI matrix points can be created by precipitation of the MALDI matrix substance from the gas phase. Precipitation from the gas phase is every process during which the MALDI matrix substance is applied from the gas phase to the surface formation. For example, condensation or sublimation are proposed. Preferably, however, the application of the MALDI matrix points to the surface formation is by sublimation. Sublimation comprises the MALDI matrix substance being transferred as a solid material to the gas phase and/or precipitated as solid material on the surface formation from the gas phase. Preferably, the sublimation takes place in a vacuum. Especially preferred is the heating of the solid material for sublimation. Preferably, for precipitation from the gas phase and especially in terms of sublimation, several MALDI matrix substances are preferably used in parallel or sequentially. The MALDI matrix substances can be used for making different MALDI matrix points. But it is also conceivable that a MALDI matrix point shows a substructure, for example partial points existing separately from each other, which are each made of a different MALDI matrix substance. A substructure can also consist of concentric annuli, each consisting of a different MALDI matrix substance.

For applying the MALDI matrix spots, a shaped body, a so-called mask with through holes, may be used which covers the sample carrier during the precipitation from the gas phase, especially preferred by way of sublimation. The MALDI matrix substance then only precipitates itself on the surface in the area of these holes and forms a MALDI matrix point or partial point there. As outlined above, preferably the MALDI matrix is deposited on the hydrophobic or even ultraphobic area. This mask can have any number of holes, which can have any shape. For example, the holes can be round, rectangular, square, triangular or oval, to name just a few of the possible shapes. The surface formation can also be initially covered by several masks, which are then removed one by one in order to, for example, apply different MALDI matrix substances to different areas of the surface formation according to the invention. Such a device and the method for depositing the microcrystalline MALDI matrix spot is described in further detail for example in US 2006/0121599, herein fully incorporated by reference. It is preferred to provide a pattern of microcrystalline MALDI matrix spots on the sample carrier in order to alleviate high throughput screening methods. Alternatively, the microcrystalline MALDI matrix spot can be obtained on the sample carrier by applying a thin-layer preparation technique, as is described in the prior art in order to pre-deposit a microcrystalline spot of MALDI matrix on the sample carrier (see e.g. Vorm et al, 1994).

A suitable sample carrier comprises an appropriate MALDI matrix such as for example α-Cyano-4-hydroxycinnamic acid (CHCA) that is pre-deposited in a patterned way on a hydrophobic, preferably an ultraphobic substrate/layer, which can deal directly as a sample support for subsequent analysis by MALDI mass spectrometry. The surface of the sample carrier can be made hydrophobic by applying an appropriate film on the sample carrier, e.g. a thiolated gold coat on a metal substrate. Also other self-assembled monolayer (SAM) structures are known in the prior art in order to obtain hydrophobic or even ultraphobic properties.

Many MALDI matrices can be used according to the method of the present invention. The MALDI matrix should be chosen such that it is capable of binding the target analyte during incubation of the complex sample on the microcrystalline MALDI matrix spot. This can be determined by simple testing. E.g. hydrophobic analytes are well bound by cinnaminic acid derivatives such as CHCA. A suitable MALDI matrix should be insoluble or nearly insoluble in the complex sample to be analysed, for example urine or serum, and the deposited pattern matrix spots on the sample carrier should preferably exhibit a crystal sizes $\leq 10$ μm, preferably $\leq 5$ μm, $\leq 2$ μm, $\leq 1$ μm. Furthermore, the used matrix shall allow the ionization of the target analyte.

The microcrystalline MALDI matrix that is pre-applied as a spot on the sample carrier used according to the present invention may have at least one of the following characteristics:

a) It contains a MALDI matrix forming compound selected from the group consisting of cinnamic acid derivatives e.g. alpha-cyano-4-hydroxycinnamicacid (CHCA), 4-chloro-alpha-cyanocinnamic acid (Cl-CCA), 3,5-dimethoxy-4-hydroxycinnamic acid (sinapinic acid (SA)), 4-hydroxy-3-methoxycinnamic acid (ferulic acid), acetophenone derivatives e.g. 2',4',6'-trihydroxy-acetophenone (THAP), carboxylic acids derivatives e.g. 2,5-dihydroxybenzoic acid, picolinic acid, 3-hydroxypicolinic acid (3-HPA), 2-(4-hydroxyphenylazo)benzoic acid, 2-aminobenzoic acid, 3-aminobenzoic acid, succinic acid, caffeic acid, nicotinic acid, adipic acid, malonic acid as well as salicylamide, isovanillin, 3-aminoquinoline, 1-sioquinolinol, dithranol, alpha-cyano-4-hydroxycoumarin acid or mixtures thereof; and/or b) It is a mixture of at least two MALDI matrix compounds; and/or c) It does not comprise nitrocellulose; and/or d) It has a crystal size of $\leq 10$ μm, preferably $\leq 5$ μm, $\leq 2$ μm, $\leq 1$ μm; and/or e) the microcrystalline MALDI matrix spot has a thickness of ≦50 µm, preferably ≦25, ≦10 µm or even ≦5 µm; and/or f) except for the MALDI matrix forming compound it does not comprise affinity capture molecules for capturing the target analyte (as are used for example in SELDI methods).

A microcrystalline MALDI matrix spot comprising predominantly crystals having a crystal size of ≦5 µm, preferably even ≦2 µm and a thickness of ≦10 µm or even ≦5 µm is particularly preferred in the method according to the present invention. As is outlined above, very homogenous MALDI matrix spots of a small crystal size can be obtained when the MALDI matrix is precipitated from the gas phase, preferably by sublimation (see above).

The method according to the present invention can be used in order to analyse various target analytes from complex samples, in particular body liquids or components thereof such as blood, plasma, serum or urine, which, albeit containing a large extent of water, consist of a plurality of components, which at physiological concentration usually prevent successful sample preparation for MALDI. Components such as salts, lipids, urea or high abundance proteins which are often present in complex samples, disturb massively the co-crystallization of matrix and analytes necessary for a reasonably MALDI performance. E.g. for a typical MALDI-MS dry droplet preparation the concentration alkali metal salts should in this context not exceed 50 mM and for urea ca. 300 mM to avoid a massive spectra degradation. Therefore, dilution of the sample in a MS compatible buffer is usually essential in the prior art methods. However, respective measures significantly decreases the limit of detection (LOD) for all target molecules and thus does not allow a defined monitoring of respective analytes, in particular in quantitative diagnostic assays. The method according to the present invention does not encounter these problems due to the unique combination of the design of the sample carrier and the method steps.

According to one embodiment, the sample applied to the matrix spot in step b) is incubated on said microcrystalline MALDI matrix spot but not dried, and the residual sample is removed after incubation before performing the washing step c). It was shown that this measure provides improved detection results, as less contaminants bind to the microcrystalline MALDI matrix spot. E.g., 1 to 50, 1 to 25 and preferably 1 to 10 µl (usually 3-5 µl) of a complex sample, e.g. a crude body fluid, can be applied directly onto the sample carrier such, that it is located on the microcrystalline MALDI matrix spot (e.g. comprising sublimated alpha-cyano-4 hydroxycinnamic acid or other cinnamic acid derivates, see above) on a hydrophobic substrate e.g. a thiolated gold-coated metal substrate. Of course, the size/amount of the droplet may vary depending on the size of the matrix spot. After a short incubation time ranging from a few seconds up to 30 minutes, optionally in an incubation chamber, the residual liquid sample is removed from the MALDI matrix spot before it dries. Alternatively, for certain applications only a very small droplet of the complex sample can be spotted directly on the microcrystalline MALDI matrix spot and completely dried down without removing the residual sample with similar results. The size of such a droplet again depends on the size of the corresponding microcrystalline matrix spot, and can be e.g. less than 500 nl, preferably less than 250 nl.

The sample is washed after it is applied to the microcrystalline MALDI matrix spot. Preferably, the microcrystalline MALDI matrix spot is washed several times (typically three times) by means of an appropriate washing solution, e.g. a aqueous ammonium citrate, ammonium phosphate or a ammonium dihydrogenphosphate solution, e.g. 20 mM, or 15 mM. According to one embodiment, the washing solution is removed before adding new washing solution and before finally drying the sample prior to analysing it by mass spectrometry.

As is outlined above, the method according to the present invention has the advantage that also complex samples and even body fluids can be analysed without the need of performing complex and laborious prior purification or separation steps. However, it is within the scope of the present invention that pre-treatment and sample preparation steps can be performed to prepare the sample for the analysis as long as the sample is after said treatment still a "complex sample" as defined above. Thus, depending on the complex sample analysed and the quantification strategy, at least one of the following upfront sample preparation steps may be performed prior to step b):

a) Centrifuging the complex sample to remove non-solved particulates; and/or b) acidifying the complex sample; e.g. to a final concentration of 0.8% trifluoroacetic acid (TFA); and/or c) adding an internal standard to the complex sample; and/or d) performing a labelling reaction in order to at least label the target analyte; and/or e) normalising the complex sample, e.g. normalisation of urine dilution to the creatinine concentration.

Respective up-front sample preparation steps are easy and quickly to perform and may further improve the obtained results depending on the complex sample to be analysed and whether and what kind of quantitative analysis is to be performed.

Different strategies for quantitation are known in the prior art, which are e.g. described in Ong (2005)) herein incorporated by reference. Subsequently, several potential quantitation strategies are described, which can be used according to the teachings of the present invention and are in particular useful for quantitating hepcidin and/or small molecules.

a) Internal standard: An appropriate internal standard can be spiked in a well defined concentration in every sample to increase the precision in relative and absolute quantitation. This internal standard deals as a reference and is used to compensate for any technical variations between individual measurements (see e.g. http://www.ionsource.com/tutorial/msquan/requantoc.htm). Typically, such an internal standard is composed of an isotopically modified target molecule (e.g. $C^{13}$ or $N^{15}$ stable isotope) or any other molecule with very similar physico-chemical properties than the target molecule. The similarity between internal standard and target molecule is needed to ensure a similar response of both molecules to any technical variation during the measurement. For example, in case the method according to the present invention is used to measure hepcidin, an isotopically modified hepcidin molecule is advantageous.

b) Labelling reaction: By performing labelling reactions (such as iTRAQ) up-front of the actual measurement it is possible to introduce a chemical label or tag to all molecules in the sample, including the target analyte, e.g. hepcidin. If different labels are used for different samples, the differentially labelled samples can be combined afterwards and measured as one combined sample (multiplexing) to increase throughput. This method can also be used e.g. to directly compare the relative abundance of the target molecule in the different samples (see also e.g. Ong (2005)).

c) Normalization for complex samples with varying dilution such as e.g. urine. E.g. creatinine normalization is typically performed to compensate for varying urine dilution and correspondingly varying target molecule concentration: If the measurement of the urine dilution is done up-front (e.g. by determining the creatinine concentration by standard clinical chemistry methods or using the method of the invention for small molecules (see below)), a normalization to a well-defined dilution or creatinine concentration can be performed by adding corresponding buffer volumes to the sample. Alternatively, the urine sample is not adjusted, but the dilution factor respectively creatinine concentration is taken into account for calculating the final target molecule e.g. hepcidin concentration of the sample.

Subsequently, mass spectra in MS mode may be acquired with appropriate acquisition methods on an MALDI-MS instrument covering the mass range of all relevant target molecules e.g. all hepcidin variants (or a target different analyte to be detected), internal standards, e.g. urinary dilution standards (e.g. creatinine) that means all urinary molecules that are helpful in the quantitation of hepcidin, in case the biological fluid is urine. Optionally, also spectra of physically or chemically induced fragments of these target molecules are acquired in MS/MS or MS$^n$ mode on the same or a separate MALDI-MS/MS or MS$^n$ instrument. Preferably, the analysis is quantitative. Mass spectrometric attributes such as peak height or peak area of all relevant target molecules in all applied MS modes can be used for relative (semi-quantitative) or absolute quantitation according to the well established procedures for mass spectrometry based quantitation (see for example Lill (2003), Ong (2005) or http://www.ion-source.com/tutorial/msquan/requantoc.htm, herein incorporated by reference).

The method according to the present invention is suitable for analysing various target analytes. The target analyte can be of any kind and may be selected from the group consisting of peptides, metabolites, drug compounds and their metabolites, oligonucleotides e.g. DNA or RNA, glycoconjugates e.g. glycoproteins, glycopeptides, peptidoglycans, glycolipids, and lipopolysaccharides as well as proteins or fragments thereof.

Typically, more than hundred peptides in the mass range from 800 to 6000 Da can be found e.g. in a urine analysis with the method according to the present invention. Some of these compounds may also provide an important diagnostic value. Applications of peptide fragments also called peptidome or fragmentome analysis and its diagnostic potential in complex samples and in particular body fluids such as e.g. urine, plasma or serum has been intensively reviewed in the prior-art (see e.g. Hortin (2006, 2007), Petricoin 2006, Schulz-Knappe (2005)), herein incorporated by reference. In brief, studies of peptide fragments may advance basic understanding of pathways for protein degradation and clearance. Endogenous peptides derived by enzymatic processes from abundant proteins are likely to be of value as indicators of systemic processes such as atherosclerosis, nutrition, stroke, major organ injury, hemostatic disorders, acute-phase responses, and kidney dysfunction but may also deliver cancer-specific diagnostic information because they are a 'recording' of the cellular and extracellular enzymatic events that take place at the level of the cancer-tissue microenvironment. Depending on the biological sample and the target peptides for analysis the invention may hence also provide a robust and quick assay method for a quantitative analysis of said peptides.

According to one embodiment the target analyte is selected from the group consisting of:
a) mature hepcidin 25, truncated hepcidin isoforms such as hepcidin-22, hepcidin-20 and/or prohepcidin; and/or
b) peptides such as, but non-limiting, endogenous peptides derived form in-vivo proteolytic processes; and/or
c) endogenous metabolites such as, but non-limiting, creatinine, amino acids, carnitines, steroids, steroid derivatives, phospholipids, organic acids, fatty acids, vitamins; and/or
d) drug compounds and their metabolites such as, but non-limiting, immunosuppressive, immunostimulator, antiretroviral, antiviral, antipsychotic, antiarrhythmic, anti-obesity, antidiabetic, antithrombotic, anticoagulant, antihemorrhagic, antihypertensive, antibiotic, antifungal, antiparasitic, anticancer, anti-inflammatory, antirheumatic, anesthetic, analgesic, anticonvulsant, psycholeptic, psychoanaleptic, antiallergic and antipruritic drugs as well as vaccines, vitamins, corticosteroids, sex hormones, thyroid hormones and/or antithyroid agents.

Human metabolites which can be analysed as target analytes are e.g. described in the Human Metabolome Database (HMDB). The HMBD is currently the most complete and comprehensive curated collection of human metabolite and human metabolism data in the world (see also Wishart et al, 2007, herein incorporated by reference). Examples of human metabolites that can be analysed by the method according to the present invention include but are not limited to Acid Amides, Acetylcarnitines, Acylglycines, Alcohol Phosphates, Alcohols, Aldehydes, Aliphatic Amines, Alkaloids, Alkanes, Alkene Phosphates, Alkenes, Alkenyl Phosphates, Alkyl Amides, Alkyl Amines, Alkyl Phosphates, Alkylthiols, Amides, Amine-Oxides, Amines, Amino Acid Phosphates, Amino Acids, Amino Alcohols, Amino Esters, Amino Ethers, Amino Phosphates, Amino Sugars, Aminoaldehydes, Aminoketones, Aromatic Acids, Aromatic Amines, Aromatic Ketones, Aromatic Phosphates, Aromatics, Aryl Chlorides, Aryl Ethers, Benzimidazoles, Biguanides, Bile Acids, Bile Alcohols, Bile Salts, Branched-chain Hydrocarbons, Carbohydrates, Carnitines, Catecholamines, Cholesterolesters, Cholesterols, Coenzyme A Derivatives, Diatomic Compounds, Diglycerides, Disaccharides, Eicosanoids, Enamines, Esters, Ethanolamines, Ethers, Fatty Acids, Fatty Alcohols, Fatty Aldehydes, Flavones, Flavonoids, Fluoroquinolones, Furancarbonitriles, Furans, Gases, Glycerols, Glycerophospholipids, Glycolipids, Glycols, Glycones, Glycosphingolipids, Guanidines, Heterocyclic Amines, Heterocyclics, Histidine Metabolites, Hydroxy acids, Imidazoles, Imides, Imino Acids, Inorganic Anions, Inorganic Gases, Inorganic Ions, Isoprenoids, Keto-Amides, Keto-Amines, Ketones, Lactams, Lactones, Lipoamides, Lipids, Lysophosphatidylcholines, Minerals, Monoglycerides, Monosaccharides, Nitrogenous Compounds, Nucleic Acids, Nucleoside Diphosphates, Nucleoside Phosphates, Nucleoside Tetraphosphates, Nucleoside Triphosphates, Nucleosides, Nucleotides, Opioids, Organic Acids, Organic Radicals, Organic Salts, Organic Sulfides, Oximes, Pentasaccharides, Peptides, Pheniramines, Phenols, Phenylacetamides, Phosphate Acids, Phosphate Amides, Phosphate Amines, Phosphate Ketones, Phosphate Thiols, Phosphatidylcholines, Phosphoamino Acids, Phosphoesters, Phosphoketones, Phospholipids, Phosphonic Acids, Polyalkalene Phosphates, Polyalkalenes, Polyamines, Polyethers, Polyketones, Polysaccharides, Porphyrins, Prostaglandins, Pterins, Purines, Pyrimidines, Quinones, Sphingolipids, Statins, Steroid Derivatives, Steroids, Sterol Esters, Sterols, Sugar Phosphates, Sugars, Sulfate Esters, Sulfonamides, Sulfones, Sulfoxides, Sulfurate Esters, Tetrapyrroles, Tetrasaccharides, Thiol Amines, Thiol Sulfates, Triglycerides, Trisaccharides and/or Vitamins.

According to one embodiment, the method is used in order to analyse hepcidin (this includes mature hepcidin 25 as well as truncated hepcidin isoforms such as hepcidin-22, hepcidin-20 and/or prohepcidin) from complex samples, in particular body fluids such as urine. Preferably, said method is quantitative. Particularly, the ease of use and speed of the method according to the present invention is outperforming other prior art approaches of hepcidin quantitation in a sample. Furthermore, the respective method allows for the first time a simultaneous measurement of hepcidin and for example a urinary dilution standard (for example creatinine) by the same method, which further accelerates the time from sample drawing to the analytical result which is very important for a diagnostic assay. Overall, the new method allows an analytical throughput (without statistical processing and/or operator based spectra interpretation) of more than 100 samples per hour. This is a great advantage over the prior art.

The method therefore allows to provide a quantitative hepcidin assay which has a sufficient limit of detection (LOD) to determine hepcidin concentrations in healthy subjects and patients suffering from hepcidin deficiencies. A hepcidin assay using the method of the present invention has at least 2 to 3 orders of magnitude linearity in quantitation, covering the range of normal and pathological hepcidin levels. As is outlined above, it also provides high throughput capabilities to measure large patients cohorts, for example in clinical studies. Furthermore, the method according to the present invention even allows the use of crude body fluids, in particular urine with no or minimal up-front sample preparation steps. This increases dramatically the throughput and on the other hand decreases the error-proneness of the overall method. Furthermore, it was shown, that the method according to the present invention has a very high specificity to detect and distinguish biological active hepcidin isoforms (for example HEPC-25) from non-active or at least less active pro-peptide and truncated hepcidin forms. Therefore, the method according to the present invention provides a high specificity and thus more reliable analytical and in particular diagnostic results. Furthermore, the method according to the present invention provides the ability to measure simultaneously but independently hepcidin and internal standards (for example isotopically labelled hepcidin). These internal standards are typically spiked in the sample at well defined concentrations and are used to compare for any technical variabilities. Suitable standards were described above.

As is outlined above, the method according the present invention is in particular suitable for measuring hepcidin (as is outlined above this includes mature hepcidin 25 as well as truncated hepcidin isoforms such as hepcidin-22, hepcidin-20 and/or prohepcidin) out of crude urine samples. This is a rather challenging task as measuring hepcidin out of crude urine must be rather robust against large different concentration of salts and urea regularly present in urine samples. Advantageously, the method according to the present invention works over large range of salt concentrations. Furthermore, the method according to the present invention allows a simultaneous but independent measurement of the urine dilution factor. The urine concentration is usually highly fluctuating between samples due to varying glomerula filtration rates. Typically, this normalization is performed by measuring urinary creatinine, which is excreted at fairly constant rates dependent only on the body muscle mass. Measuring the creatinine concentration allows to normalize all samples to a well defined creatinine concentration, for example by buffer addition or by calculating the obtained HEPC intensities with respect to the individual creatinine concentrations. The urinary HEPC concentration is hence given usually as peak intensities or area per mMol creatinine. Furthermore, the method according to the present invention is even able to measure hepcidin from sample volumes of less than 50 µl, and thus for example allows urinary hepcidin measurements in animal models, such as for example rodent models.

Furthermore, the method according to the present invention is suitable for measuring hepcidin (as is outlined above this includes mature hepcidin 25 as well as truncated hepcidin isoforms such as hepcidin-22, hepcidin-20 and/or prohepcidin) out of blood samples, in particular serum and/or plasma. As is outlined herein, the complex samples can be prepared for analysis by pre-treatment steps, including but not limited to centrifugation.

An assay using the method according to the present invention thus simultaneously combines in particular MALD-MS based quantitation with unique on probe sample clean-up and hepcidin enrichment properties of a patterned microcrystalline matrix layer. Particularly, the ease of use and speed of the analysis is outperforming other approaches to hepcidin quantitation.

Furthermore, an assay using the method according to the present invention allows to clean up, detect and distinguish minute amounts of small molecules such as endogenous metabolites or administered drugs or drug metabolites, directly from complex samples such as crude body liquids e.g. serum or urine, without any labour intensive and time consuming up-front sample preparation, in particular prior purification and/or separation of the sample. In the method according to the present invention, this feature is purposefully combined with the high throughput capability of a pattern of such pre-deposited microcrystalline matrix spots. The method according to the present invention therefore allows to abandon classical and laborious up-front sample preparation techniques used for example in LC-MS/MS as described above. The method according to the present invention is a selective and sensitive analytical method for the quantitative evaluation of drugs and their metabolites (analytes). Sensitivity and selectivity are critical requirements for successful conduct of preclinical and/or biopharmaceutical and clinical pharmacology studies. Non-limiting application examples for such analysis are given in the examples and figures section below.

Also provided with the present invention is a diagnostic assay, wherein the method according to the present invention is performed. In particular, a diagnostic hepcidin assay is provided. Also provided is a diagnostic assay for monitoring small molecules, in particular endogenous metabolites, drug compounds and their metabolites in a body fluid, wherein the method according to the present invention is performed. Suitable details regarding the method and the assay are described above and also apply to the diagnostic assay according to the present invention.

The invention also provides the use of a sample carrier comprising a pre-applied layer of a microcrystalline MALDI matrix spot which is at least partially encompassed by a hydrophobic region in a method according the present invention which is described in detail above. Details regarding the design of the sample carrier and its preparation are described in detail above and also apply herein.

All references mentioned herein are incorporated by reference and thus form part of the disclosure. The present invention is subsequently described by the non-limiting examples and figures, which describe, however, preferred embodiments of the invention.

FIGURES/EXAMPLES

FIG. 1

One embodiment of the method according to the present invention relies on the protocol depicted in FIG. 1, which is in particular suitable for performing an peptide assay e.g. for hepcidin or for measuring drugs or drug metabolites as target analytes. The general protocol can be divided into optional up-front sample preparation steps (a) and b)), which are carried out typically in a microliter or milliliter vial or tube and on-chip (sample carrier) protocol steps, which are carried out directly on the sample carrier, which comprises the microcrystalline MALDI matrix spots, pre-applied on the hydrophobic surface of the sample carrier. The sample carrier used in the example shown in FIG. 1 is a QIAGEN MassSpecTurbo Chip, which is commercially available.

In step a) the complex sample (10 µl-5 ml, typically 50 µl) is prepared. The complex sample may be a crude body fluid, such as plasma, serum, urine, CSF. Up-front sample preparation steps involve e.g. centrifugation (e.g. 5 minutes at 5,000× g) for complex samples containing particulates and acidification e.g. of crude urine e.g. by adding 0.2 mL TFA (5% v/v) to 1 mL urine.

Consecutively, in step b) further optional protocol steps can be performed, which e.g. depend on the preferred quantitation strategy. Different strategies for quantitation are known in the prior art, and are described above.

E.g. an internal standard may be added, a labelling reaction may be performed or the creatinine concentration may be normalized.

In FIG. 1 c) a detail of the sample carrier is shown, namely a microcrystalline matrix spot pre-applied on a hydrophobic surface. In steps d) to g) all consecutive on-chip protocol steps of the method according to the present invention are described. These steps comprise the manual or automatic application of preferably 1-10 µl complex sample (typically 3-5 µl)—which may be prepared as described above—directly on the microcrystalline MALDI matrix spot (FIG. 1d)). After a short incubation time of usually a few seconds to 30 minutes (typical 3-5 minutes) the residual sample is removed (FIG. 1e)). After a drying step of approximately 1-2 minutes or more e.g. at ambient air, the MALDI matrix spot is washed several times (typically three times) by means of an appropriate washing solution, e.g. 15 mM aqueous ammonium dihydrogenphosphate solution (FIG. 1f)). Subsequently, the sample may be dried and the sample carrier is inserted into a MALDI mass spectrometer for detection and quantitation of e.g. hepcidin-25 and its isoforms (FIG. 1g)).

FIG. 2

Figure 2:
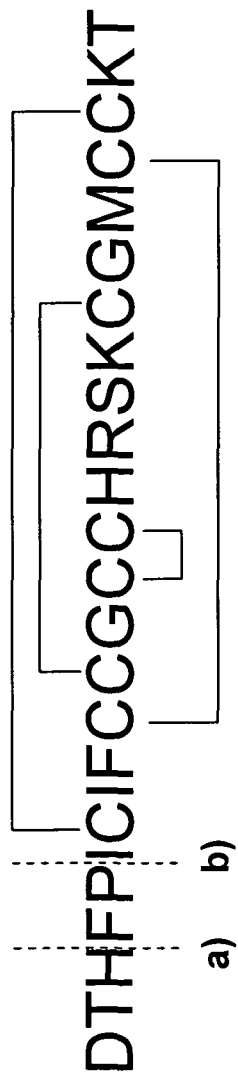

FIG. 2 shows the amino acid sequence of hepcidin 25 (SEQ ID NO. 1). Disulfide bridges and the molecular weight are indicated. Also the truncated isoforms hepcidin 22 (a)) and hepcidin 20 (b)) are indicated (SEQ ID NOs. 2 and 3).

FIG. 3

Figure 3:
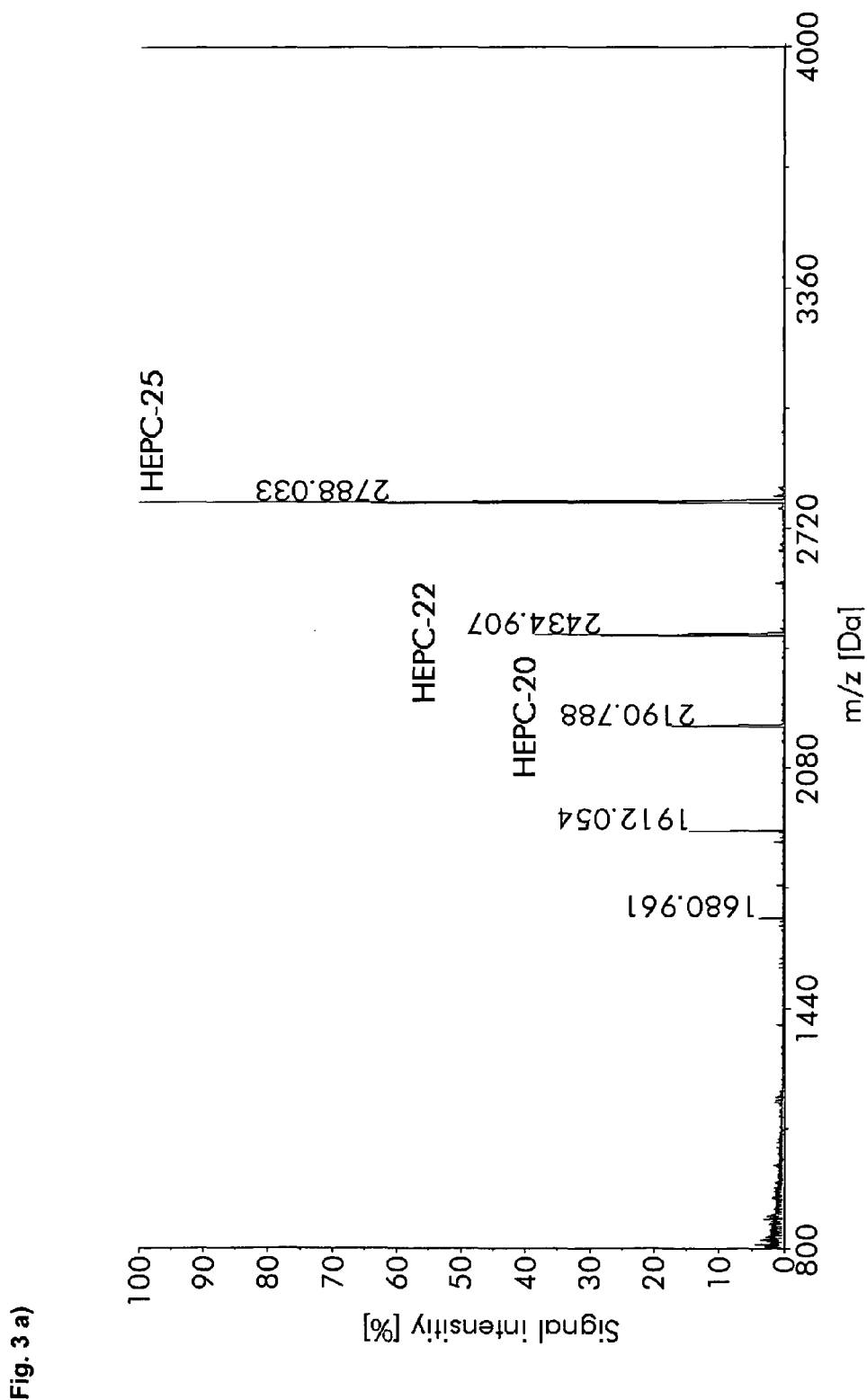
Figure 3:
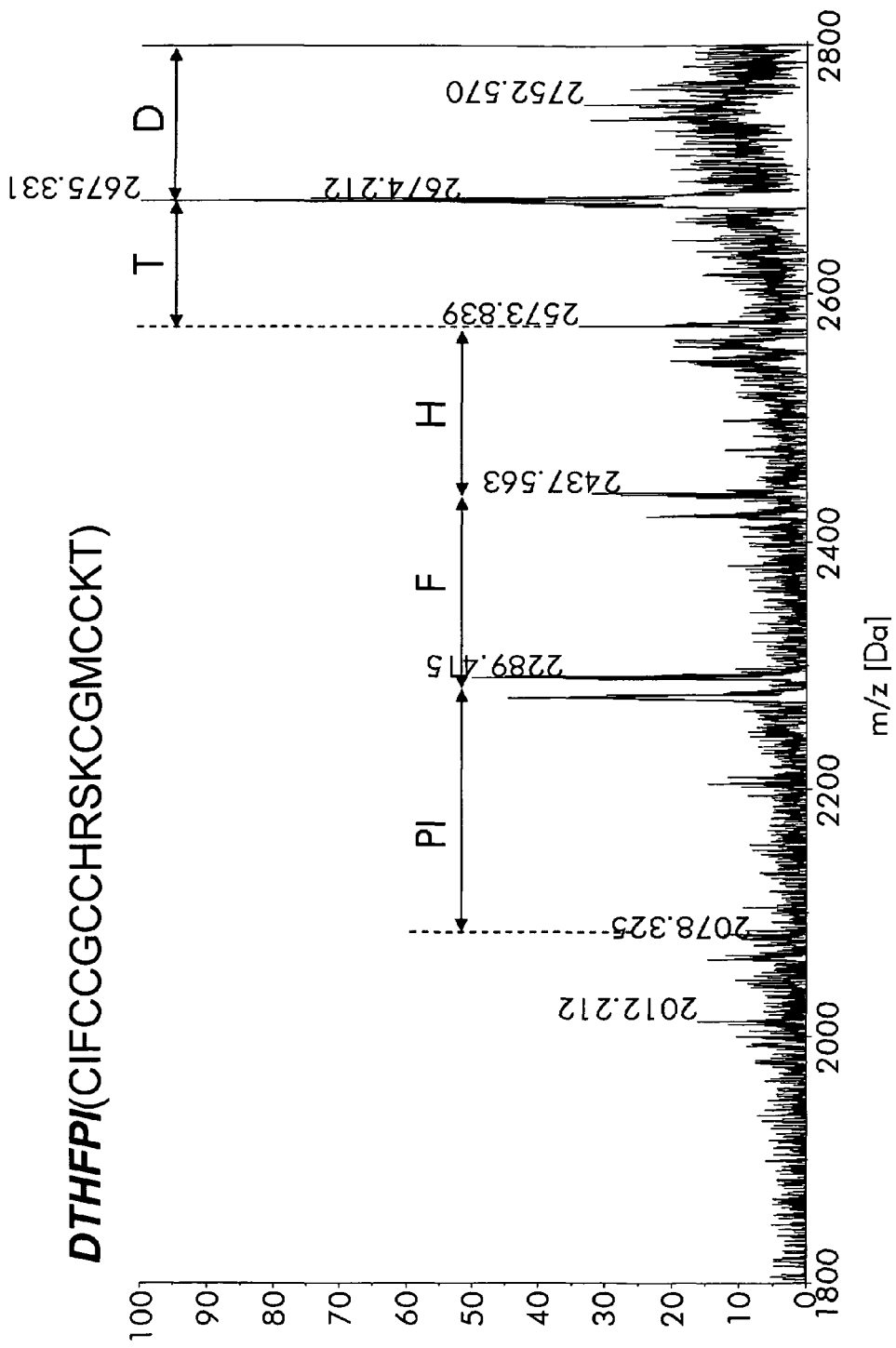
Figure 3:
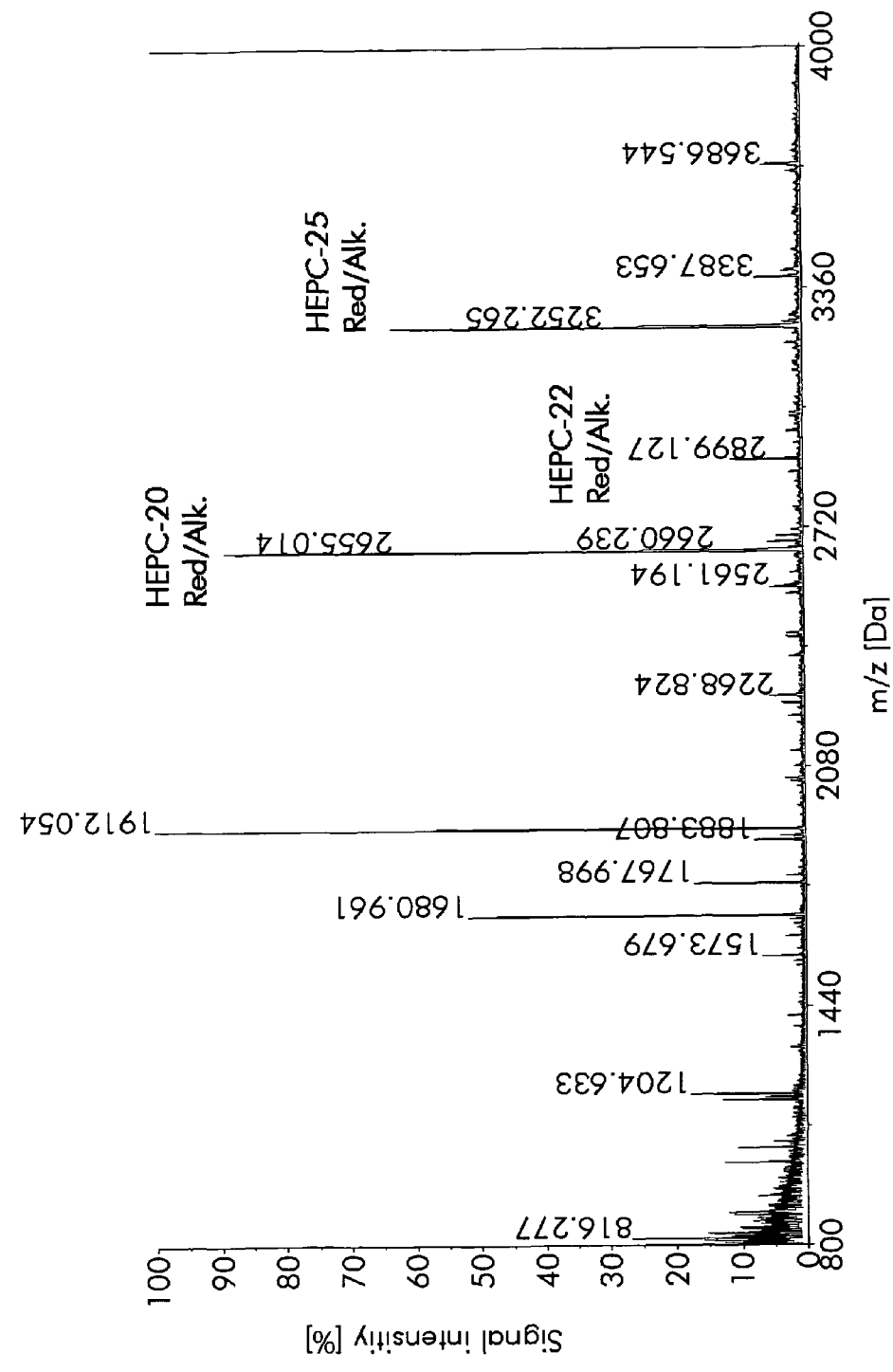

The unambiguous detection of endogenous HEPC by the method according to the present invention is shown in FIG. 3. FIG. 3 a) depicts a mass spectrum from crude urine obtained with the method according to the present invention on a MALDI-TOF mass spectrometer in reflector mode. The corresponding signal peaks of the three different Hepcidin isoforms (HEPC-25, HEPC-22 and HEPC-20) are clearly visible in the spectrum and are accordingly labelled.

FIG. 3 b) shows an MS/MS spectrum of HEPC-25 (SEQ ID NO 1) from which an N-terminal sequence tag of 4 consecutive amino acids (DTHF—SEQ ID NO 4) and one amino acid pair (PI) could be derived (marked in bold in FIG. 3b). With this sequence tag and the accurate mass of the precursor, an unambiguous identification of HEPC-25 from the SwissProt database using the MASCOT sequence query search algorithm was obtained. To validate this identification the urine sample was reduced and alkylated and the mass shift of all HEPC peaks was monitored.

FIG. 3 c) shows that this mass shift (8×58 Da=464 Da) corresponds to the expected reduction and carboxyamidomethylation by iodoacetamide of the 8 cysteines in HEPC.

FIG. 4

Figure 4A:
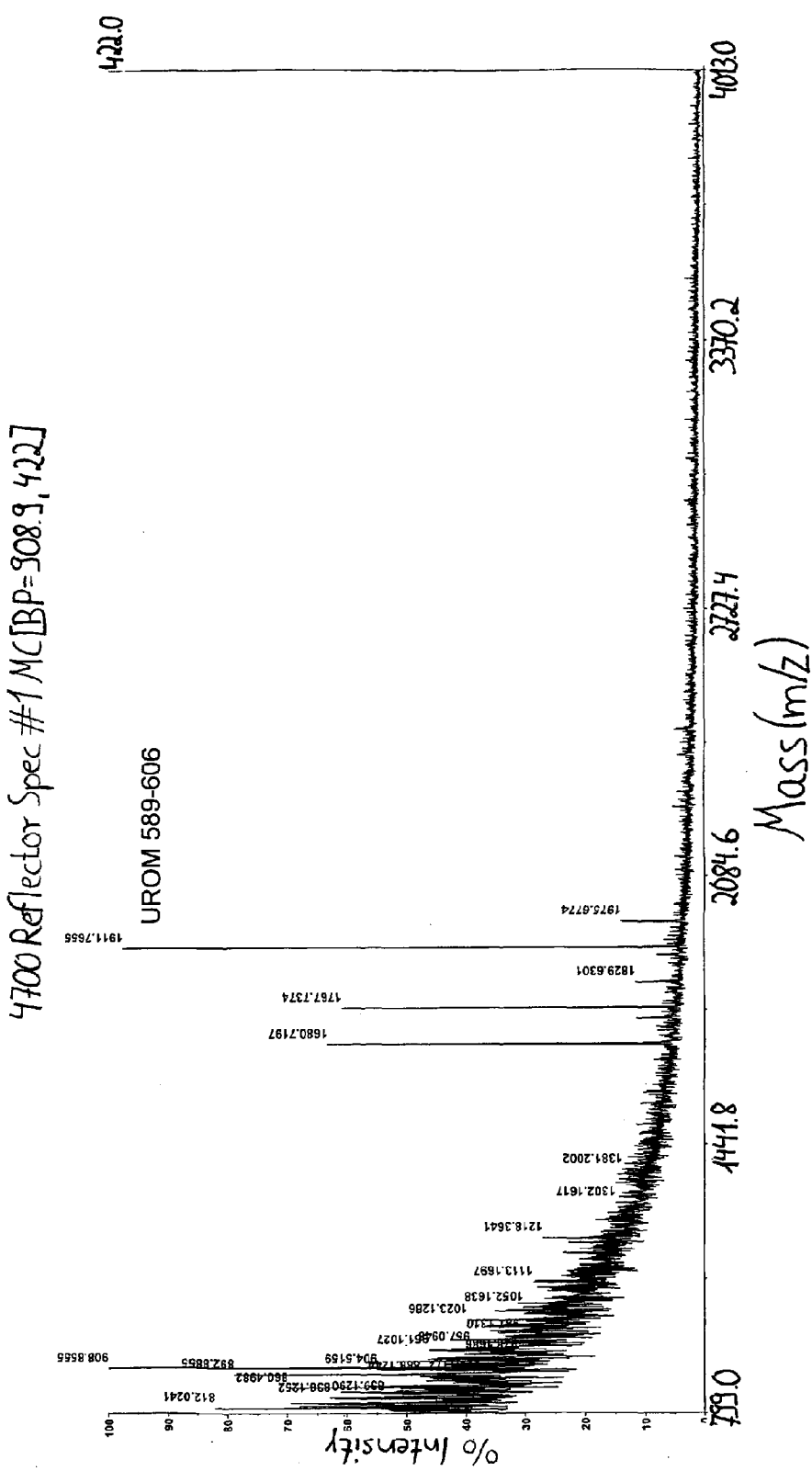
Figure 4B:
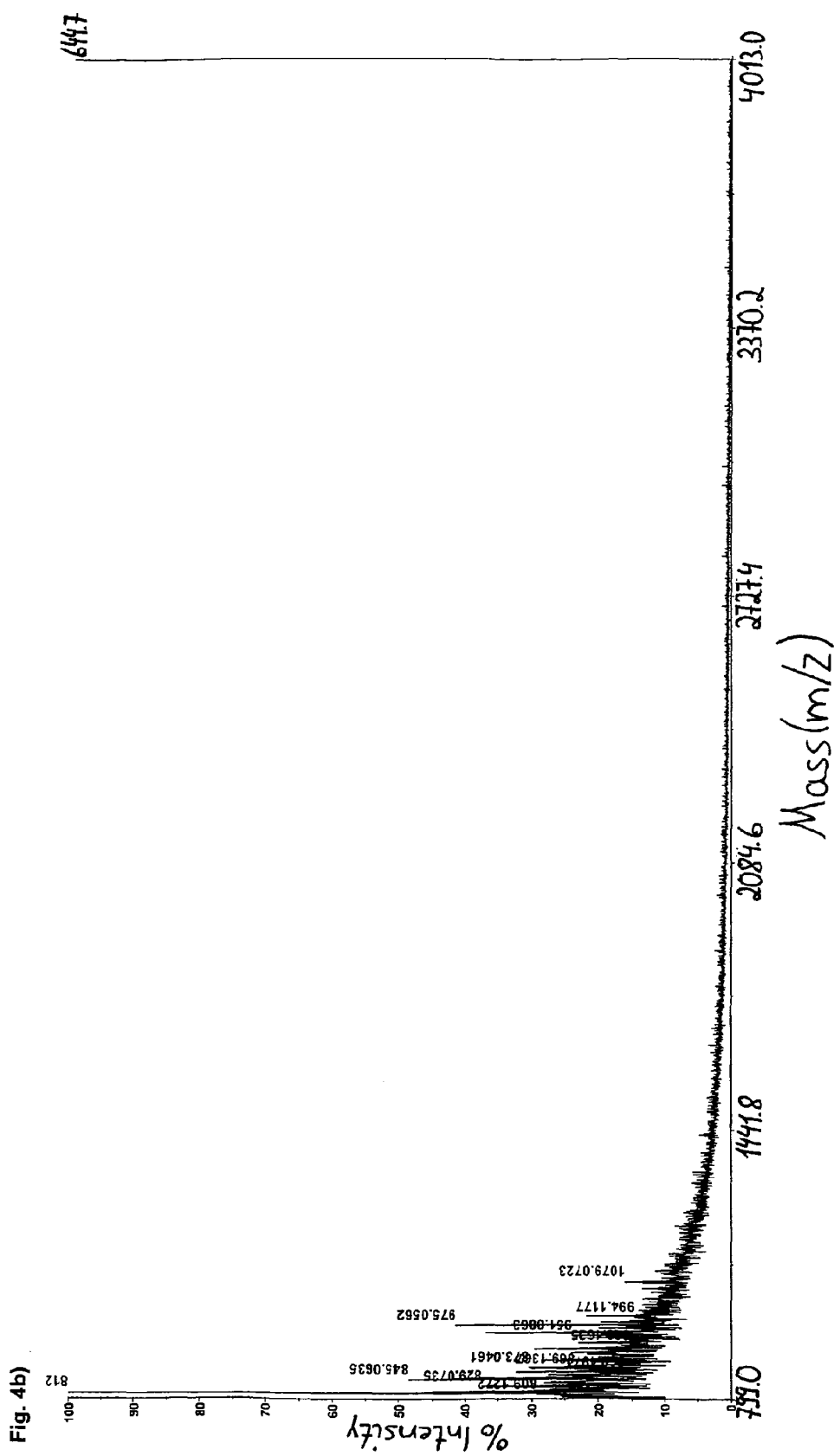
Figure 4C:
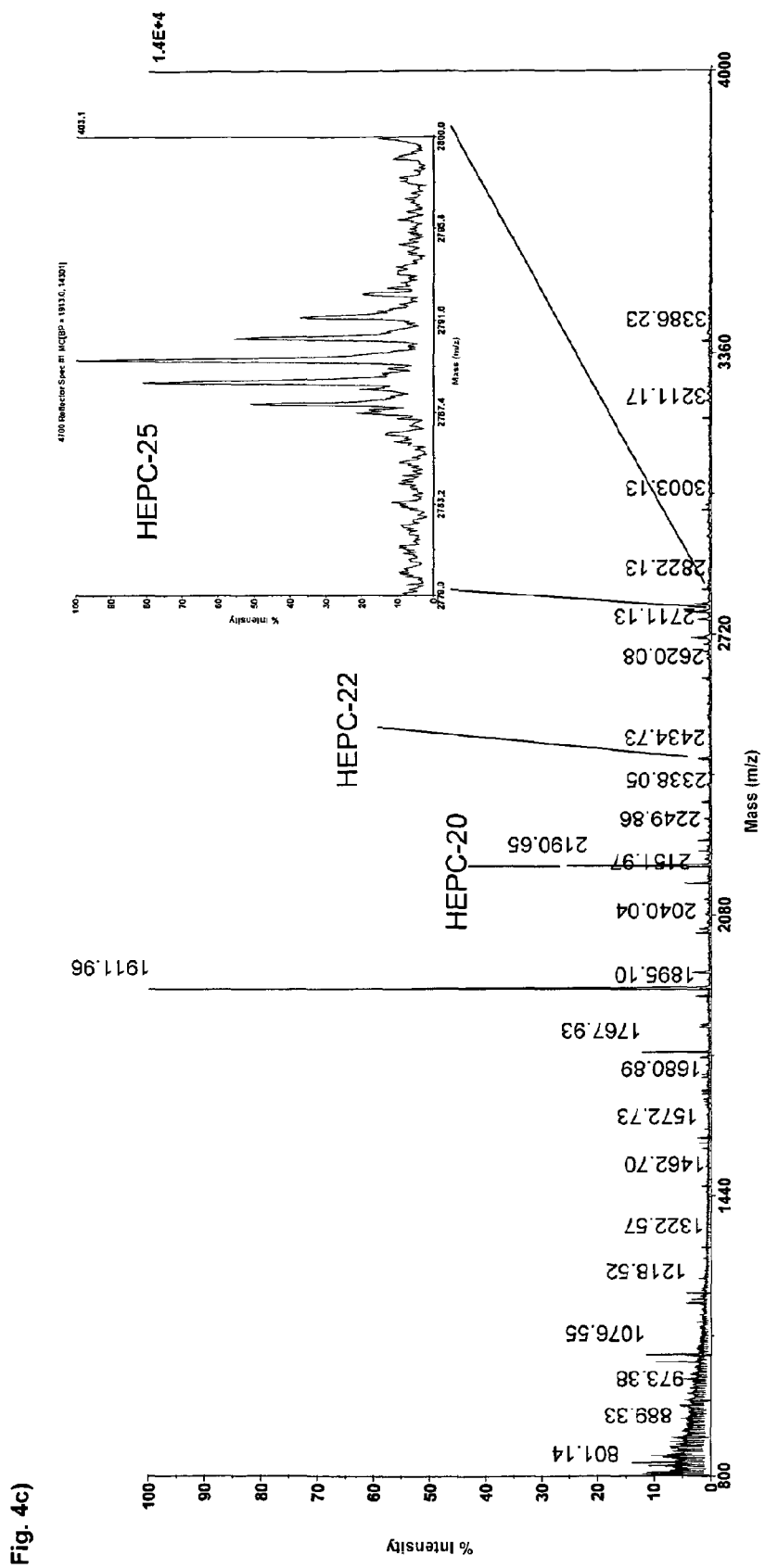
Figure 5A:
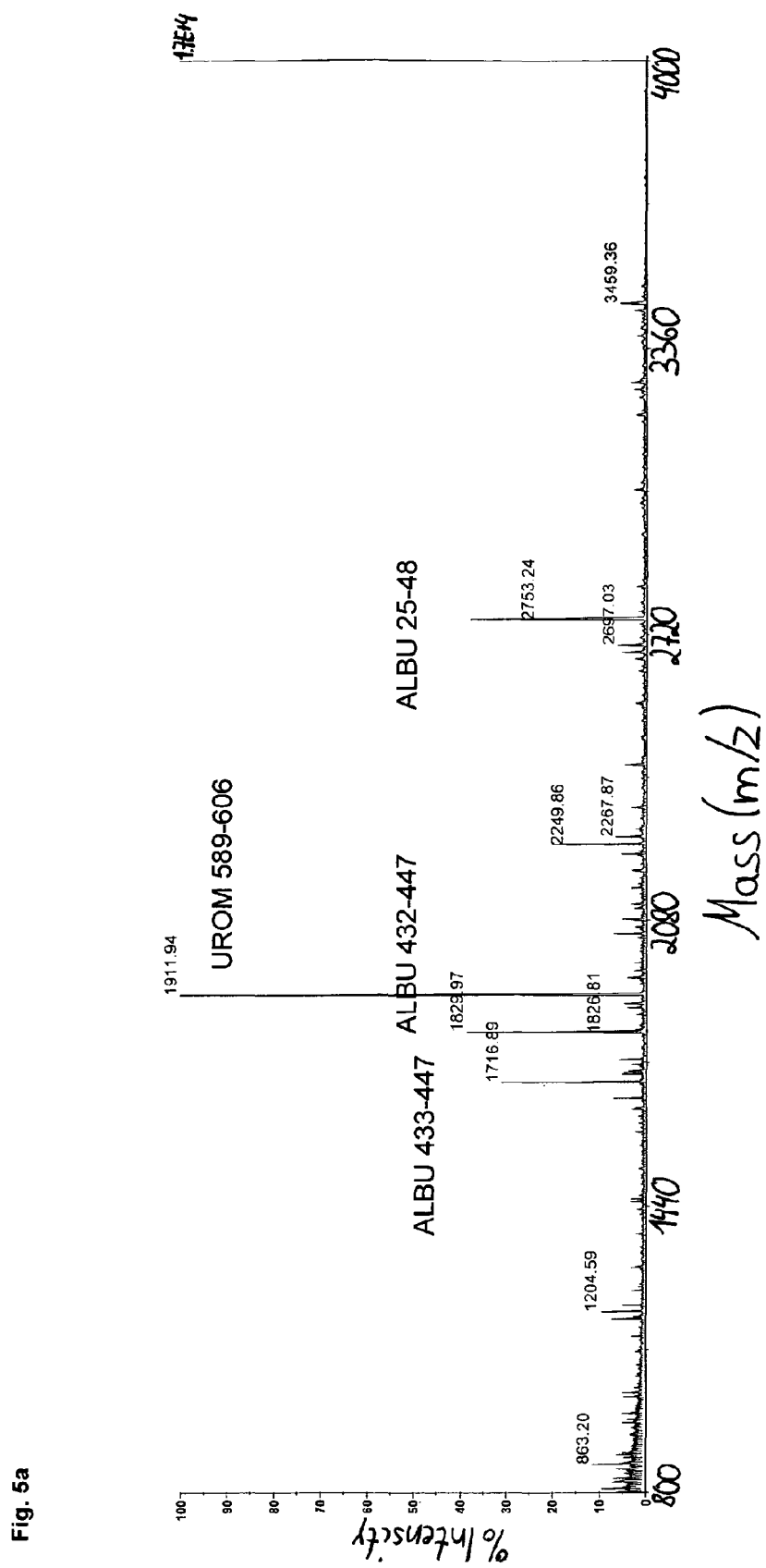

FIG. 4 demonstrates the performance of HEPC detection according to the method of the present invention compared to a standard dried droplet MALDI preparation technique as is commonly applied in the prior art. A crude urine sample with lower hepcidin concentrations than in FIG. 3 was used. For the dried droplet method (FIG. 4 a) and b) the sample and the matrix solution are mixed in a vial or directly on the MALDI sample support, which yields crystal sizes typically larger than 10 µm. Without diluting the crude urine sample no mass spectrum could be obtained at all, as various contaminations of urine such as salt and urea prevent crystallization of the matrix crystals completely. FIG. 4 a) was obtained by using the dried droplet sample preparation technique with a ten times diluted urine sample resulting again in crystals typically larger 10 µm. After dilution several endogenous urinary peptides such as uromodulin fragments (see also FIG. 5a) are detectable in FIG. 4 a) but no HEPC-25 or its isoforms. The overall spectra quality in FIG. 4a) is low as can be deduced by the low signal intensity and the low signal/noise ratios for the non-HEPC peaks. In FIG. 4 b) the dried droplet method was combined with additional washing steps (here 3 times). This resulted however in a complete removal and/or suppression of all peaks. Similar results (data not shown) were obtained if a matrix preparation according to the dried droplet method was pre-spotted on the target and the urine sample was applied consecutively and treated equally to the protocol of the method according to the present invention. The methods of the prior art are thus unsuitable to measure hepcidin in urine.

With the method according to the present invention, which uses a microcrystalline layer (crystal sizes preferably <1 µm) of a pre-applied matrix spot, strong hepcidin related peaks (HEPC-20, HEPC-22 and HEPC-25 (zoom)) could be detected with this urine sample as is shown in FIG. 4 c). Beside HEPC related peaks also other peaks originating from endogenous peptides are detectable with the method according to the present invention and reveal a much stronger signal intensity and signal/noise ratio compared e.g. to the prior-art depicted in FIGS. 4a+b). This demonstrates the superior performance of the method for the analysis of complex samples according to the present invention.

FIG. 5

Figure 5B:
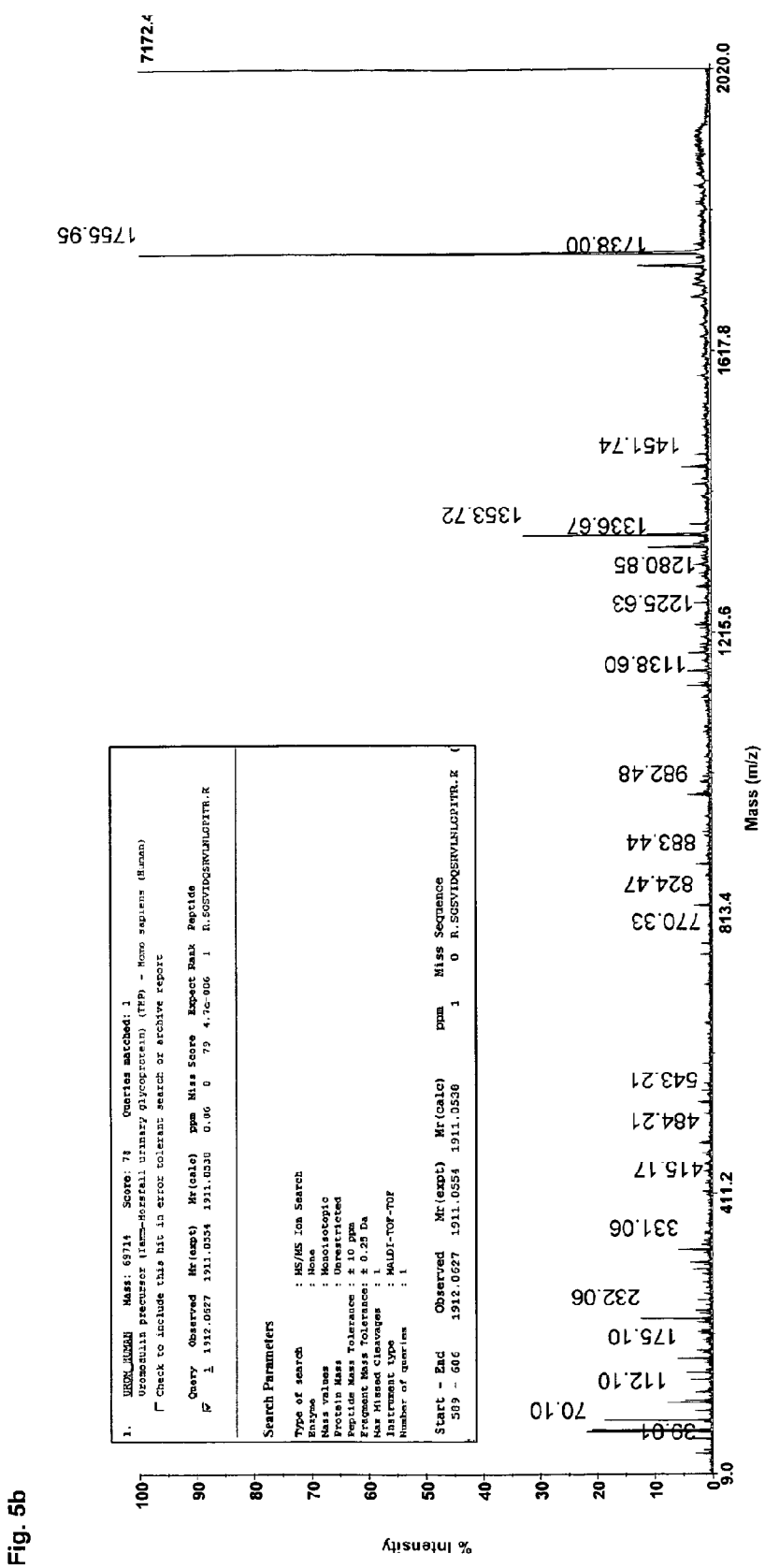

In FIG. 5 a), a spectrum is shown obtained with the method according to the present invention for crude urine with a very low HEPC concentration. Here, the non-HEPC related peaks are more pronounced. For some of the more abundant peaks sequence identification was performed by means of MALDI-MS/MS experiments. FIG. 5 b) shows exemplarily the MS/MS spectrum of an abundant fragment (SEQ ID NO 5) derived from uromodulin (Tamm-Horsfall urinary glycoprotein). The insert in FIG. 5b) shows the search parameters and the result from the corresponding MS/MS search using the MASCOT search algorithm unambiguously identifying UROM_HUMAN 589-606 in the SwissProt database. Mainly endogenous urinary peptides from abundant proteins such as fragments of human albumin (e.g. ALBU_HUMAN 433-447: VRYTKKVPQVSTPTL (SEQ ID NO 6) (1716 Da), ALBU_HUMAN 432-447: LVRYTKKVPQVSTPTL (SEQ ID NO 7) (1830 Da) or ALBU_HUMAN 25-48: DAHKSEVAHRFKDLGEENFKALVL (SEQ ID NO 8) (2753 Da)) or of uromodulin (e.g. UROM_HUMAN 589-606 (1912 Da)) or several collagen fragments (data not shown) could be obtained. Typically, more than hundred non-hepcidin related peptides in the mass range from 800 to 6000 Da can be found in each urine analysis with the new method. Some of these compounds may also provide diagnostic value comparable to the assay described for hepcidin. Applications of peptide fragments also called peptidome or fragmentome analysis and its diagnostic potential in e.g. urine and plasma/serum has been intensively reviewed in the prior-art and are discussed above. Depending on the biological sample and the target peptides for analysis the invention may hence also provide a high-throughput assay method for a quantitative analysis of said peptides.

FIG. 6

Figure 6:
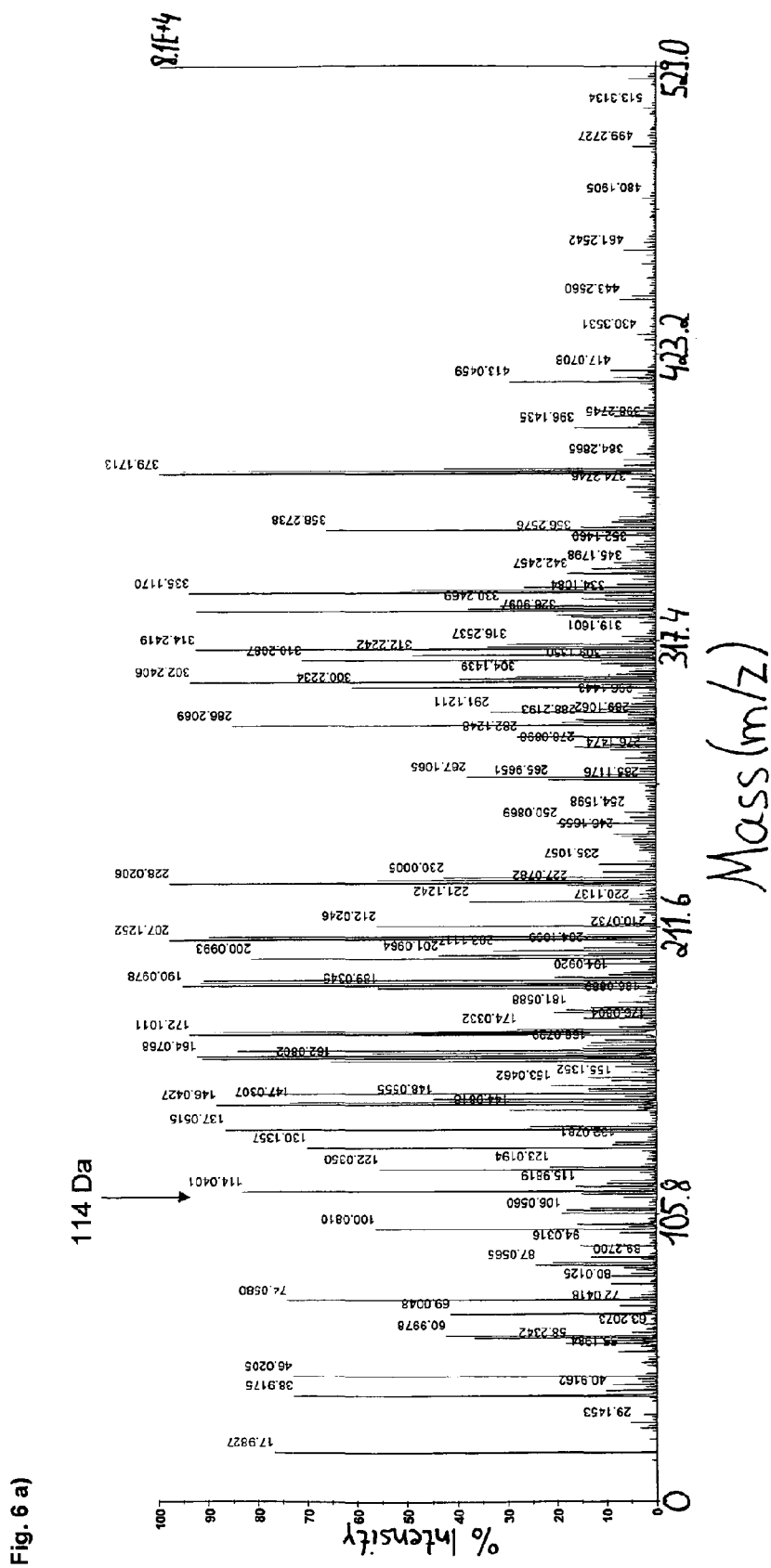
Figure 6:
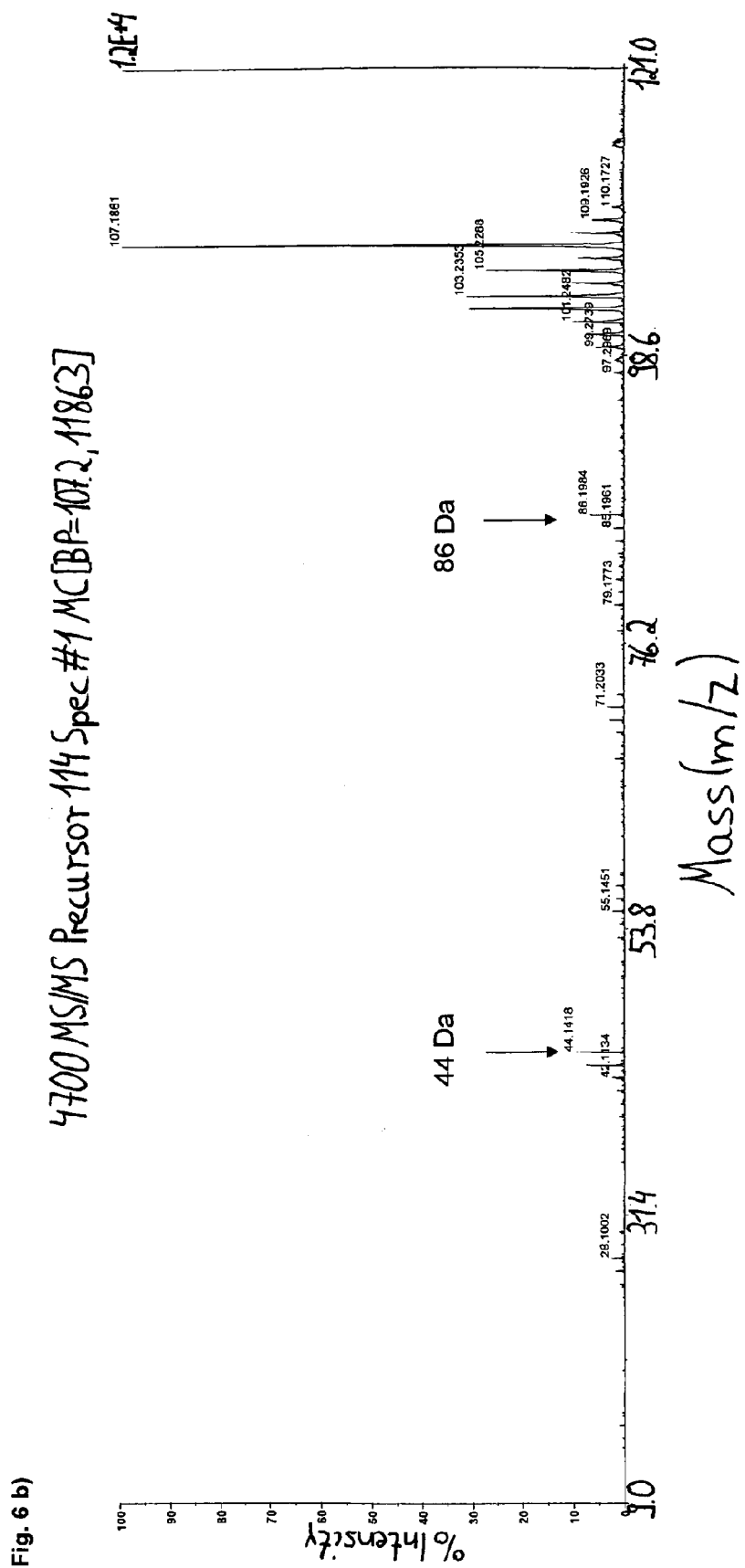

Even more peaks are evident in the mass range of small molecules and peptides below 800 Da, as shown in FIG. 6 a). These peaks are related to urinary metabolites such as amino acids but also peaks related to the MALDI matrix itself. Particularly interesting is the marked peak at 114 Da, which could be identified as urinary creatinine according to the MS/MS pattern of FIG. 6 b), showing characteristic fragments at 44 Da and 86 Da (see e.g. the LC-MSMS spectra shown in Huskovaa (2004) or Takashi (2007)). For quantitating the creatinine concentration with the new method a stable isotope modified creatinine molecule as an internal standard similar to the approach by Huskovaa and Takashi can be used. It should be pointed out here that the new method allows to measure from the same sample both the target HEPC molecules and the intrinsic urine dilution factor creatinine, which would tremendously speed up the overall HEPC quantitation process, respectively sample throughput and time-to-result. The creatinine measurement otherwise must be done separately by a different assay based either on a modified Jaffe's method, in which picric acid forms a colored solution in the presence of creatinine or by a enzymatic colorimetric method.

As is outlined above, the method according to the present invention allows to monitor a greater range of endogenous metabolites. For human metabolites an inventory of such metabolites was published recently by Wishart (2007)) and http://www.hmdb.ca/herein incorporated by reference.

FIG. 7

Figure 7:
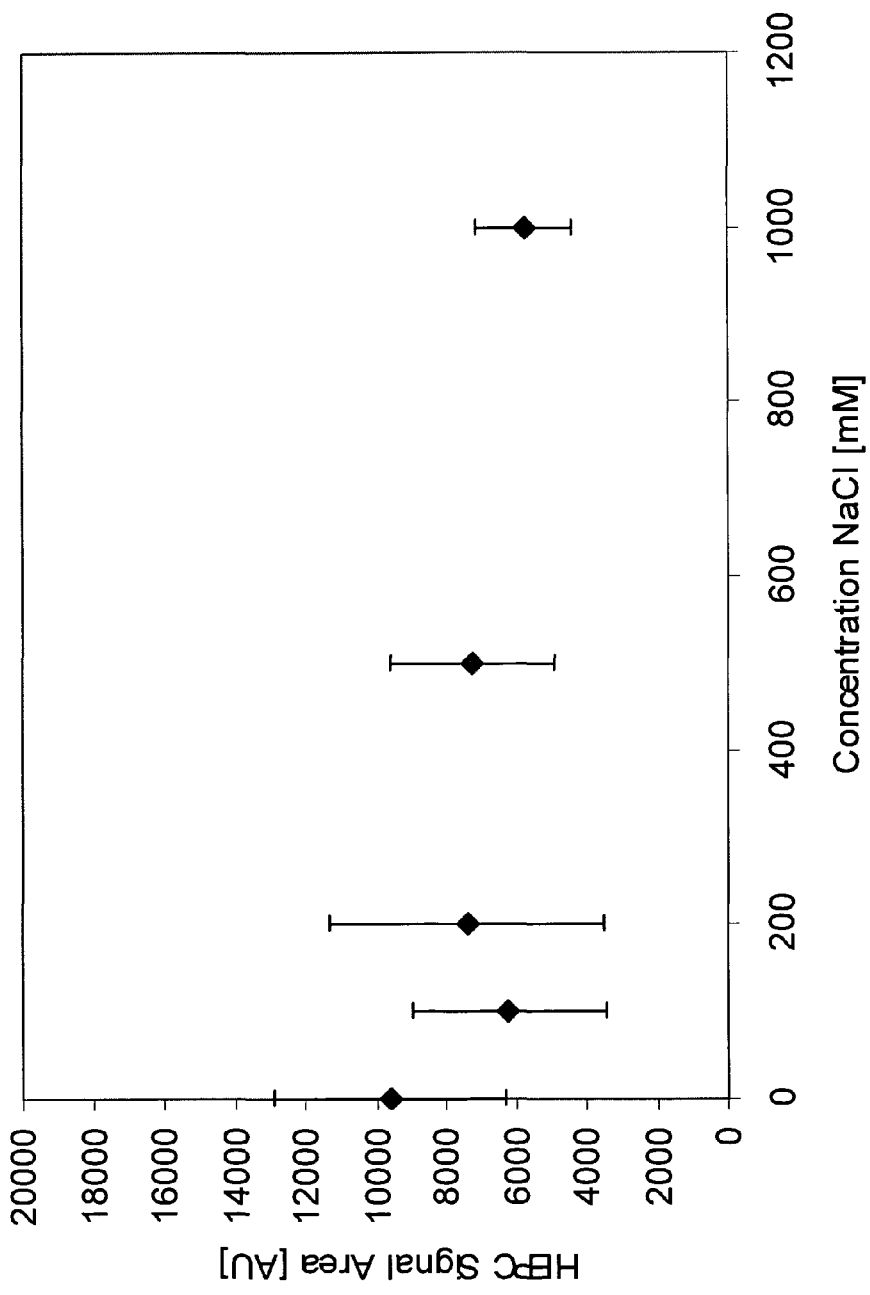
Figure 7:
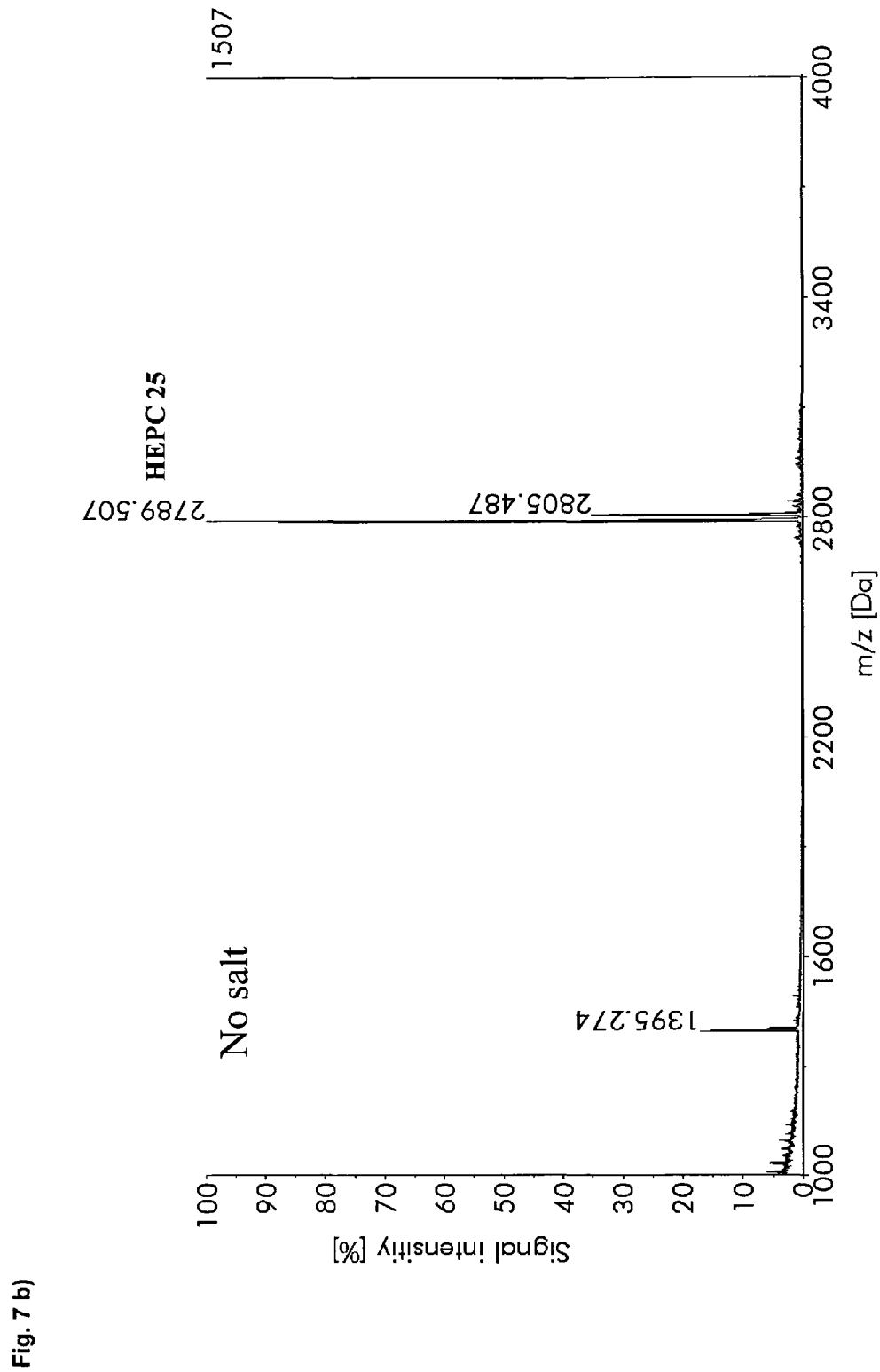
Figure 7:
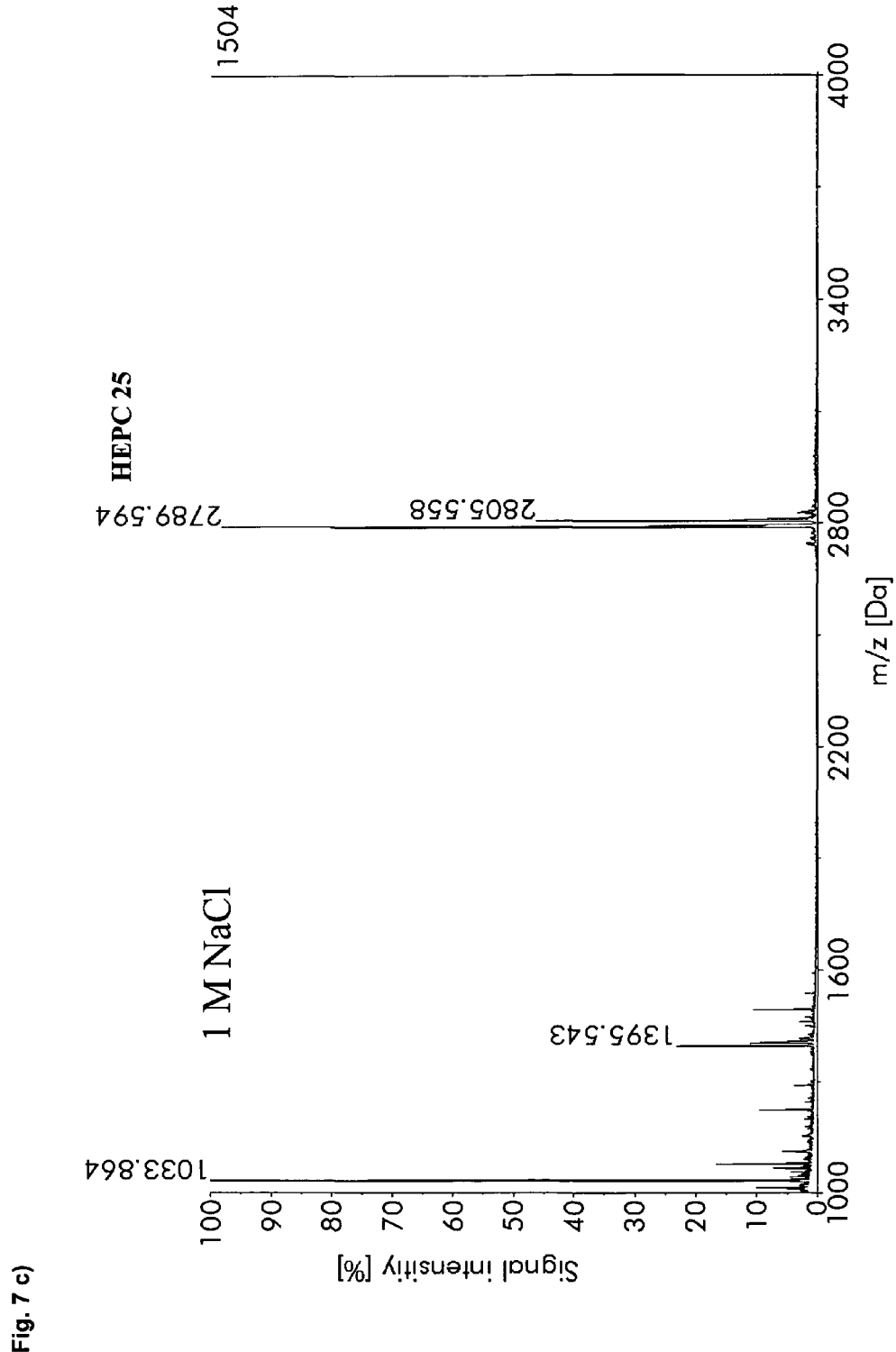

FIG. 7 a) to c) demonstrate the robustness of hepcidin detection on varying salt concentrations with the method according to the present invention. 50 pg synthetic HEPC25 was spiked in various concentrations of NaCl buffers and analyzed according to the new method. Even high salt loads up to 1M do not significantly disturb mass spectrometric performance when using the method according to the present invention. Apparently, a robust binding between hepcidin and the applied CHCA matrix is responsible for this behavior.

FIG. 8

Figure 8:
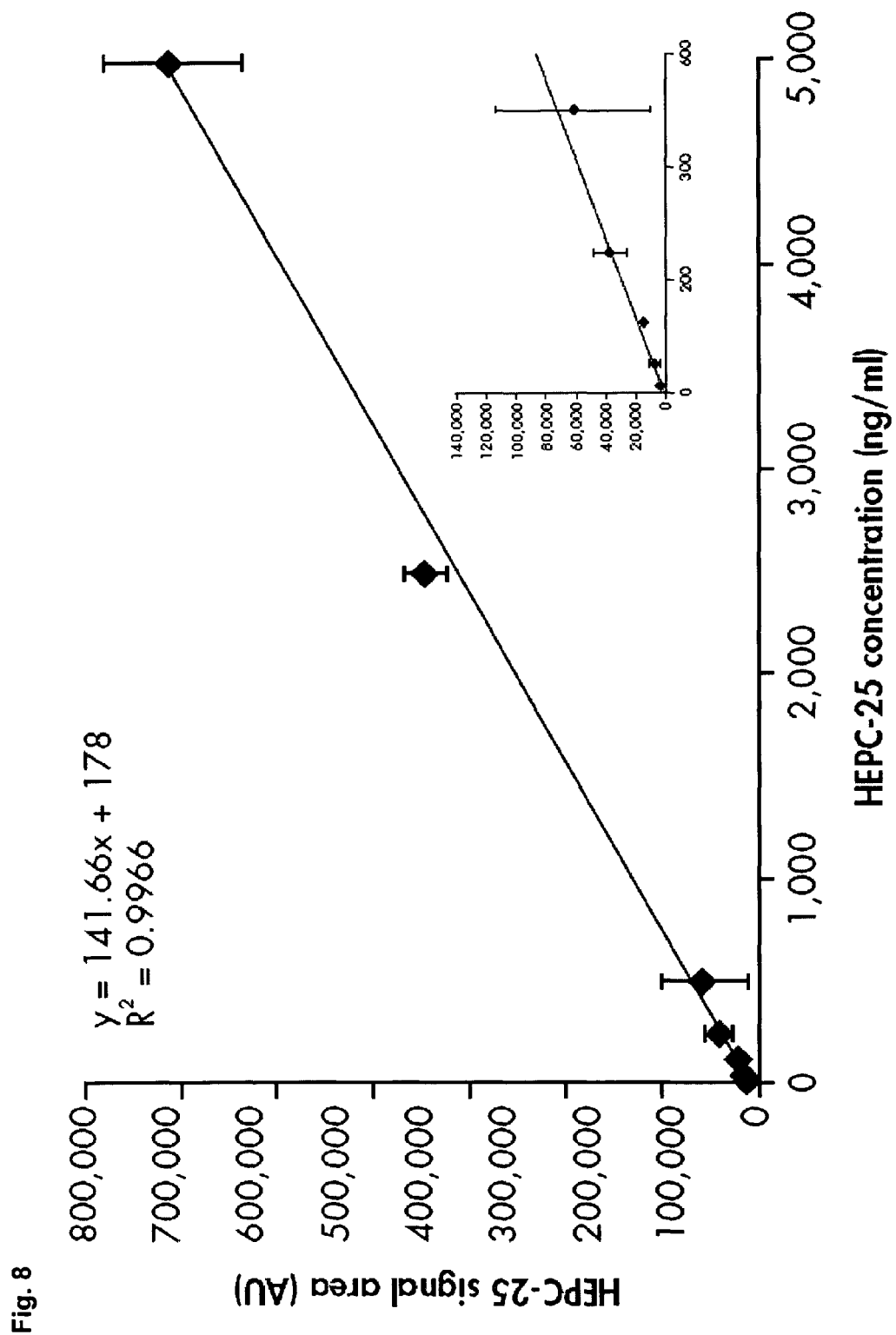

FIG. 8 shows the linear response of the HEPC-25 peak area in dependence of the HEPC-25 urine concentration for a dilution series of synthetic HEPC-25 in human urine with the method according to the present invention. The x-axis indicates the HEPC-25 concentration [ng/ml], the y-axis the peak area HEPC-25 [arbitrary units, a.u.]. Within this preliminary experiment already an LOD in the range of 5-10 ng/ml and a reasonable linearity between 10 ng/ml and 5000 ng/ml could be established. These results can be further improved. A corresponding linear regression yielded the given linear equation with a good squared correlation coefficient $R^2=0.9966$. This equation can deal as the basis of a calibration curve (often called standard curve) for HEPC quantitation from urine samples with unknown hepcidin concentrations. An urine dilution factor (e.g. creatinine) should be taken into account for accurate quantitation of different samples.

FIG. 9

Figure 9:
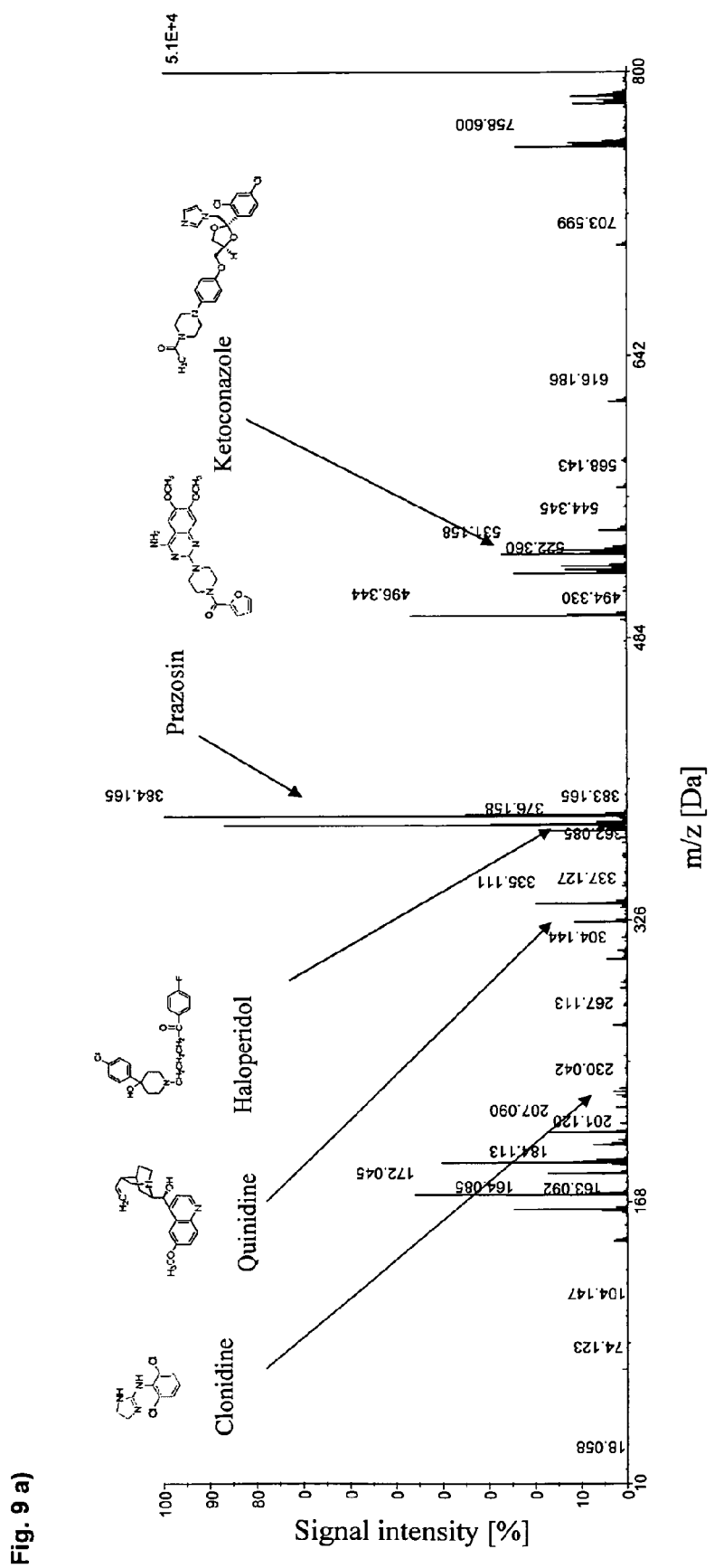
Figure 9:
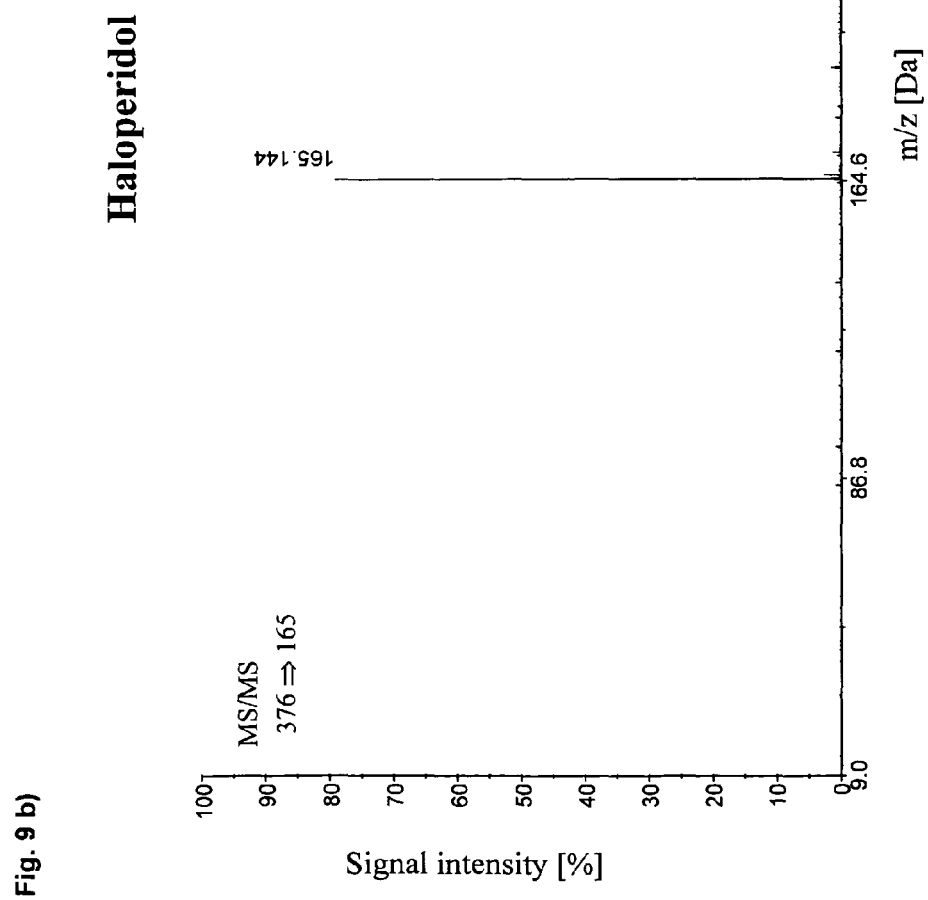

FIG. 9 a) shows the analysis of five typical drug compounds out of serum using the method according to the present invention. The alpha-adrenergic blocker Clonidine and Prazosin, which lower blood pressure by relaxing blood vessels, as well as the antipsychotic drug Haloperidol, the antiarrhythmic agent Quinidine and the antifungal drug Ketoconazole were spiked at a concentration of 1 ng/µl each in a non-diluted human serum sample. All compounds are easily detectable in MS mode (see FIG. 9a). The identity of all compounds was verified by MS/MS experiments detecting characteristic fragments (transitions) of the different compounds as exemplarily shown in FIG. 9 b) for Haloperidol (165 Da fragment of the 376 Da precursor ion) and 9 c) for Ketonacole (489 Da fragment of the 532 Da precursor ion). No spectra could be obtained with the same spiked serum and a dried droplet MALDI preparation method according to the prior art. This demonstrates the advantages of the method according to the present invention over the prior art.

FIG. 10

Figure 10:
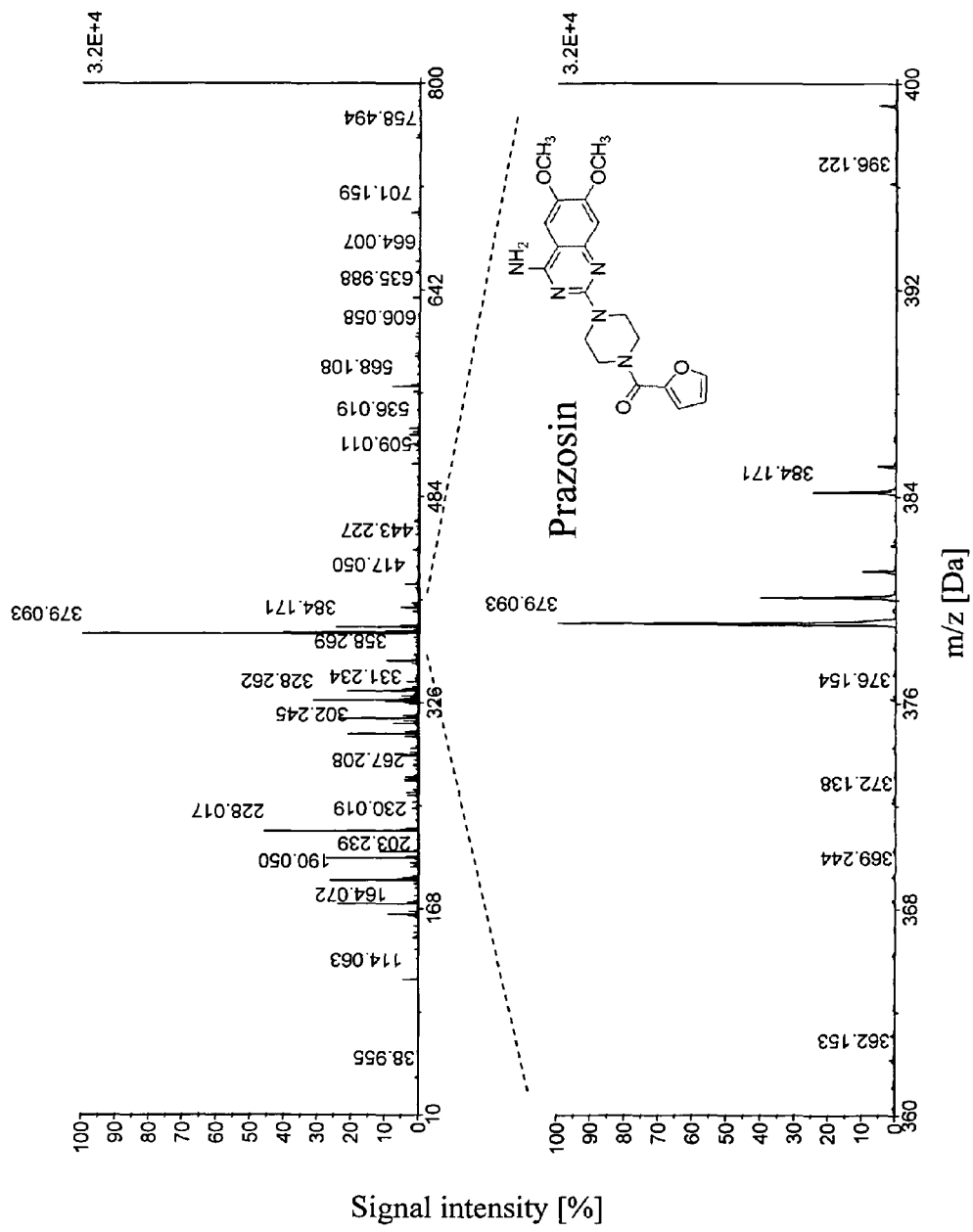
Figure 11:
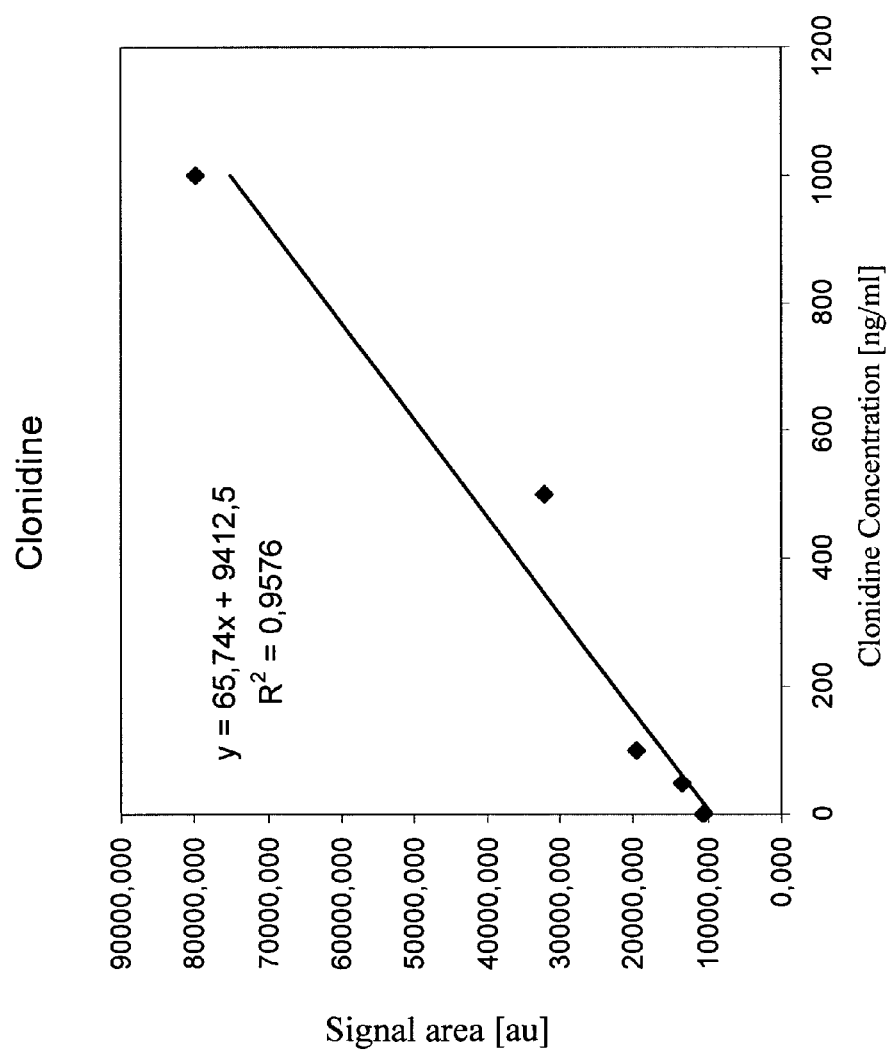

FIG. 10 shows the detection of Prazosin directly from crude urine with the method according to the present invention at a concentration of 50 pg/µl spiked in a crude urine sample. The x-axis indicates the marks [m/z], the y-axis the signal intensity [%]. A zoom in (lower panel) shows that the Prazosin 384 Da peak (FIG. 10 b)) is clearly distinguishable from the CHCA Matrix dimer background peak at 379 Da. The analysis of the same compound with a standard dried droplet preparation failed, as the sample did not crystallize out of crude urine. This demonstrates the advantages of the method according to the present invention over the prior art.

FIG. 11

Shown is a calibration curve or standard curve for the drug clonidine spiked at different concentrations in human serum analogous to FIG. 8 for hepcidin in urine. The Y-axis indicates the peak area [a.u.]. Within this preliminary experiment already an LOD in the range of 10 ng/ml and a reasonable linearity between 10 ng/ml and 1000 ng/ml could be established. These results can be further improved.

REFERENCES

Huškováa (2004)): Hušková R. Chrastina, P. Adam, T. Schneiderka, P. Clinica Chimica Acta, 350, 2004, 99-106
Kemna (2005b): Kemna, E. Tjalsma, H. Laarakkers, C. Nemeth, E. Willems, H. Swinkels D., Blood, 106, 2005, 3268-3270
Kemna (2007): Kemna E H J M, Tjalsma H, Podust V N, Swinkels D W. Clin Chem 2007; 53:620-628
Kemna (2008): Kemna, E. H. J. M.; Tjalsma, H.; Willems, H. L.; Swinkels, D. W.; Haematologica, 93, 2008, 90-97
Malyszko (2007): Malyszko, J. and Mysliwiec, M., Kidney Blood Press Res, 30, 2007, 15-30
Ong (2005): Ong S E, Mann M. Nature Chemical Biology, 1, 2005, 252-262.
Takashi (2007): N Takahashi, G Boysen, F Li, Y Li, J A Swenberg, Kidney International, 71, 2007, 266-271.
Tomosugi (2006): Tomosugi N, Kawabata H, Wakatabe R, Higuchi M, Yamaya H, Umehara H, et al., Blood 2006; 108:1381-1387
Vorm (1994): Vorm, O. Roepstorff, P. Mann, M., Analytical Chemistry, 66, 1994, 3281-3287
Lill (2003): Jennie Lill; Mass Spectrometry Reviews, 2003, 22, 182-194
Ward (2008): Ward, D G, Roberts, K. Brookes, M J Joy, H. Martin, A. Ismail, T. Spychal, R. Iqbal, T. Tselepis, C. World J Gastroenterol; 2008; 14(9): 1339-1345
Want (2005): Elizabeth J. Want, Benjamin F. Cravatt, and Gary Siuzdak; ChemBioChem 2005, 6, 1941-1951

Maurer (2005): Hans H. Maurer, Clin Biochem. 2005 April; 38(4):310-318

Petricoin (2006): Emanuel F. Petricoin, Claudio Belluco, Robyn P. Araujo, Lance A. Liotta Nature Reviews Cancer 6, 2006, 961-967

Hortin (2006): GL Hortin, Clin Chem. 2006 July; 52(7): 1223-37

Hortin (2007): GL Hortin, D Sviridov; Pharmacogenomics, 8, 2007, 237-255

Schulz-Knappe (2005): P. Schulz-Knappe, M. Schrader, H D Zucht, Combinatorial Chemistry & High Throughput Screening, 8, 2005, 697-704

Wishart (2007): D S. Wishart et al., Nucleic Acids Res. 2007 January; 35(Database issue): D521-D526

The invention claimed is:

1. A mass spectrometry method for analysing the presence or absence and/or quantity of at least one target analyte in a complex sample, wherein the complex sample:
   i) is or is derived from urine, blood, serum, or plasma;
   ii) comprises more than 50 different compounds; and
   iii) comprises more than 100 mM salt and/or urea,
   and wherein the target analyte is selected from the group consisting of mature hepcidin 25, truncated hepcidin isoforms and prohepcidin, the method comprising at least the following steps:
   a) providing a sample carrier suitable for mass spectrometry comprising a pre-applied microcrystalline matrix-assisted laser desorption/ionization (MALDI) matrix spot which is at least partially encompassed by a hydrophobic region, and wherein the microcrystalline MALDI matrix spot comprises crystals having predominantly a crystal size of $\leq 2$ μm;
   b) applying a complex sample such that it becomes located on said microcrystalline MALDI matrix spot, wherein the complex sample;
      i) is or is derived from urine, blood, serum or plasma;
      ii) comprises more than 50 different compounds; and
      iii) comprises more than 100 mM salt and/or urea;
   c) washing said sample on said microcrystalline MALDI matrix spot with a washing solution; and
   d) analysing said sample for the presence or absence of at least one target analyte selected from the group consisting of mature hepcidin 25, truncated hepcidin isoforms and prohepcidin via mass spectrometry.

2. The mass spectrometry method according to claim 1, wherein the target analyte is mature hepcidin 25.

3. The mass spectrometry method according to claim 1, wherein the complex sample:
   a) is or is derived from urine;
   b) comprises more than 100 different compounds; and
   c) comprises more than 300 mM salt and/or urea.

4. The mass spectrometry method according to claim 1, wherein the microcrystalline MALDI matrix spot
   a) comprises crystals having predominantly a crystal size of $\leq 1$ μm; and
   b) is obtained by a sublimation process.

5. The mass spectrometry method according to claim 1, wherein in step b) said sample is incubated on said microcrystalline MALDI matrix spot but not dried, and the residual sample is removed after incubation before performing the washing step c).

6. The mass spectrometry method according to claim 1, wherein the washing solution is removed, the sample is dried and then analysed in step d).

7. The mass spectrometry method according to claim 1, wherein the microcrystalline MALDI matrix has at least one of the following characteristics:
   a) is selected from the group consisting of cinnamic acid derivatives, alpha-cyano-4-hydroxycinnamic acid (CHCA), 4-chloro-alpha-cyanocinnamic acid (Cl-CCA), 3,5-dimethoxy-4-hydroxycinnamic acid (sinapinic acid (SA)), 4-hydroxy-3-methoxycinnamic acid (ferulic acid), acetophenone derivatives, 2',4',6-trihydroxyacetophenone (THAP), carboxylic acids derivatives, 2,5-dihydroxybenzoic acid, picolinic acid, 3-hydroxypicolinic acid (3-HPA), 2-(4-hydroxyphenylazo) benzoic acid, 2-aminobenzoic acid, 3-aminobenzoic acid, succinic acid, caffeic acid, nicotinic acid, adipic acid, malonic acid, salicylamide, isovanillin, 3-aminoquinoline, 1-sioquinolinol, dithranol, alpha-cyano-4-hydroxycoumarin acid and mixtures thereof;
   b) is a mixture of at least two MALDI matrix compounds;
   c) does not comprise nitrocellulose;
   d) the microcrystalline MALDI matrix spot has a thickness of $\leq 50$ μm; and
   e) the microcrystalline MALDI matrix spot is deposited on a hydrophobic surface.

8. The mass spectrometry method according to claim 1, wherein the complex sample is prepared for the analysis by at least one of the following steps:
   a) centrifuging the complex sample;
   b) acidifying the complex sample;
   c) adding an internal standard to the complex sample;
   d) performing a labelling reaction in order to at least label the target analyte in the complex sample; and
   e) normalisation of the complex sample.

9. The mass spectrometry method according to claim 1, wherein the analysis is quantitative.

10. The mass spectrometry method according to claim 1, wherein the complex sample is blood.

11. A diagnostic assay for analysing at least one target analyte, wherein the method according to claim 1 is performed.

12. A diagnostic assay according to claim 11, wherein the target analyte a mature hepcidin 25.

* * * * *